(12) United States Patent
Saumarez

(10) Patent No.: US 7,945,315 B2
(45) Date of Patent: May 17, 2011

(54) SYSTEM FOR ANALYSIS OF ELECTROGRAMS

(75) Inventor: Richard Saumarez, Waterbeach (GB)

(73) Assignee: Medilec Limited, Devon (GB)

( * ) Notice: Subject to any disclaimer, the term of this patent is extended or adjusted under 35 U.S.C. 154(b) by 276 days.

(21) Appl. No.: 12/306,572

(22) PCT Filed: Jun. 29, 2007

(86) PCT No.: PCT/EP2007/056579
§ 371 (c)(1),
(2), (4) Date: Feb. 9, 2009

(87) PCT Pub. No.: WO2008/000821
PCT Pub. Date: Jan. 3, 2008

(65) Prior Publication Data
US 2009/0227884 A1    Sep. 10, 2009

(30) Foreign Application Priority Data
Jun. 29, 2006    (GB) .................................. 0612932.4

(51) Int. Cl.
*A61B 5/04*    (2006.01)
(52) U.S. Cl. ...................................................... 600/523
(58) Field of Classification Search .................. 600/523, 600/510, 515; 607/5, 9, 14
See application file for complete search history.

(56) References Cited

U.S. PATENT DOCUMENTS

| | | | |
|---|---|---|---|
| 6,748,261 B1 | 6/2004 | Kroll et al. | |
| 6,792,307 B1 | 9/2004 | Levine et al. | |
| 2002/0165586 A1 | 11/2002 | Hill et al. | |
| 2003/0074026 A1* | 4/2003 | Thompson et al. | ............. 607/14 |
| 2005/0075673 A1 | 4/2005 | Warkentin et al. | |

FOREIGN PATENT DOCUMENTS
WO    WO 94/02201    2/1994

OTHER PUBLICATIONS

Saumarez et al., "Paced Ventricular Electrogram Fractionation and Sudden Death in Hypertrophic Cardiomyopathy and other Non-coronary Heart Diseases," Cardiovascular Research, vol. 47, pp. 11-22, 2000.

(Continued)

*Primary Examiner* — George Manuel
*Assistant Examiner* — Robert N Wieland
(74) *Attorney, Agent, or Firm* — BainwoodHuang

(57) ABSTRACT

A system for use in analysis of electrograms comprising: an input signal generator (302); an input electrode (304) for applying an input signal to a driving region of a heart (316); an output electrode (306*a-c*) for receiving an output signal at a driven region of the heart; a processing system (300) operable to receive signals indicative of said recorded value from the output electrode for analysing conduction paths through the heart, wherein the signal generator is operable to generate an input signal comprising a plurality of pulses, being spaced from each other by a pacing interval; and the processing system being arranged to identify signal delay between the input signal and the output signal on the basis of the signal received by the output electrode in relation to the plurality of pulses, and to identify a rate of variation in signal delay over a range of values of pacing interval.

14 Claims, 21 Drawing Sheets

OTHER PUBLICATIONS

Saumarez et al., "Primary Ventricular Fibrillation is Associated with Increased Paced Right Ventricular Electrogram Fractionation," Circulation, vol. 92, pp. 2565-2571, 1995, downloaded from http://circ.ahajournals.org/cgi/content/full/92/9/2565 on Oct. 13, 2006.

Tai et al., "Prolonged Fractionation of Paced Right Atrial Electrograms in patients with Atrial Flutter and Fibrillation," Journal of the American College of Cardiology, vol. 37, pp. 1651-1657, 2001.

International Search Report for PCT/EP2007/056579, mailed on Apr. 25, 2008.

United Kingdom Search Report for GB0612932.4, mailed on Oct. 16, 2006.

* cited by examiner

19 Controls
32 SCD patients studied following VF.

210 patients studied by EP.
32 SCD patients studied following VF.

210 patients studied by EP.
32 SCD patients studied following VF.

Test positive dead = 9
Test positive alive = 14
PPA = 0.39 (0.19-0.59)

SYSTEM FOR ANALYSIS OF ELECTROGRAMS

FIELD OF THE INVENTION

The present invention relates to systems for use in performing and analysing electrograms, in particular for the identification of a cardiac condition.

BACKGROUND OF THE INVENTION

As is known in the art a human heart comprises pacemaker cells and cardiac muscle cells (myocardium). Cardiac muscle cells are stimulated to contract by an electrical signal. An incident electrical signal causes a cardiac cell to undergo depolarisation. The cell slowly repolarises after it has been stimulated in this way. A contraction in a cardiac muscle cell causes changes to the environment of a neighbouring cell, which can trigger contraction in the neighbouring cell. In this way a signal is transmitted through the muscle of the heart.

In the resting state cells are negative (having a resting potential of about −70 mV). When a muscle cell is stimulated the potential inside increases (i.e. becomes less negative), in a process known as "depolarisation". Once the cell has depolarised it slowly repolarises.

Furthermore, all heart muscle cells are self-stimulating. This is due to the fact that they slowly depolarise by themselves, in the absence of any stimulating current. However, in a normal heartbeat the stimulation of the heart muscle cells is regulated by a pacemaker cell in the heart. The pacemaker cell is also self-stimulating (i.e. it also depolarises by itself), but the period of this depolarisation is faster than that of the heart muscle cells, so that in a normal heartbeat the muscle cells are stimulated by the action of the pacemaker cell before the muscle cells spontaneously depolarise. When the pacemaker cell depolarises it transmits an electrical signal to the heart muscle cells, which are then stimulated in an ordered manner (the wave of stimulation is started by pacemaker cells, and passes through the heart as the stimulated muscle cells stimulate neighbouring muscle cells). The ordered stimulation of the heart muscle means that the heart contracts, pumping blood around the body. Once a heart muscle cell has been stimulated it cannot be stimulated again for certain time known as the refractory period (this is related to the time taken for the cell to repolarise sufficiently to be stimulated again).

An arrhythmia (or dysrhythmia) occurs where the muscles of the heart quiver, and the normal rhythm of the heart muscles is disrupted. A fibrillation is an example of a serious arrhythmia, where there is a lack of coordination of the contraction of the muscle tissue of the large chambers of the heart. A fibrillation can be affect an atrium of the heart (atrial fibrillation (AF)), or a ventricle of the heart (ventricular fibrillation (VF)). Ventricular fibrillation tends to be a more serious cardiac condition than atrial fibrillation, since the ventricles of the heart pump the blood to the body, and to the lungs.

VF is a cause of sudden cardiac death (SCD) which can affect apparently healthy individuals. Certain cardiac conditions pre-dispose people to VF. Furthermore, post-coronary patients, i.e. patients who have had a heart attack, for example a coronary thrombosis which has lead to myocardial infarction (AMI or MI) and scarring of the muscle tissue of the heart, may also be at risk of VF. Heart conditions such as hypertropic cardiomyopathy (HCM), dilated cardiomyopathy (DCM) congestive heart failure (CHF) and long QT syndrome (LQTS) pre-dispose people to VF. Therefore, these people are at risk of SCD, and it is desirable to determine high-risk patients so that they can be treated accordingly (such as by inserting an implantable defibrillator).

People with HCM have fibrosis and disarray in the myocardium, which are likely to create delays dues to tortuous conduction, and local block effects; further, the tissue shows an increase in transverse propagation. LQTS patients show a longer QT period on the ECG. In LQTS there is normal myocardial architecture, but these patients may still be prone to VF, depending on their LQTS phenotype.

An important phenomenon relating to fibrillation is that of re-entry. Re-entry basically involves a muscle cell being stimulated twice by one electrical impulse sent by the pacemaker cells. The muscle cell is stimulated once, becomes refractory, repolarises and is then stimulated again after its refractory period has elapsed. Re-entry may be caused by disruption in the heart substrate, such as by scar tissue, for example.

An example of disruption of conduction through a heart having conduction blocks such as those seen in HCM patients will now be described with reference to FIGS. 1 to 8.

FIG. 1 is a schematic diagram showing a heart following a previous heart beat, such that an area of the heart is still refractory. The heart myocardium 10 has an area of homogenous tissue 12, and an area of fibrous tissue 14. FIG. 1 shows potential conduction paths through the homogenous tissue, represented by straight lines 16, and indicating rapid conduction paths. In contrast, the conduction paths through the fibrous tissue region 14 are shown as twisted and curved, denoted by lines 18, indicative of slower conduction paths in this region. There is a region (hereafter called "the region 20") which effectively has a prolonged refractory period 20. The region 20 receives the signal passing through the homogeneous tissue 12, and the delayed signal passing though fibrous tissue 14. This means that the area is refractory following a previous heart beat.

FIG. 2 is a schematic diagram showing an activation front 22 of conduction for the next heart beat through myocardium. FIG. 2 shows the region 20 which is still refractory following the last beat. As shown in FIG. 3, the activation front 22 advances until it reaches the region 20, which, being refractory, cannot be stimulated by the activation front 22, and the activation front 22 deflects around the region 20 (see FIG. 4). As can be seen in FIG. 4, part of the activation front enters the fibrous tissue region 14, whereupon part of the wavefront slowly advances though the conduction paths 18 in the fibrous tissue 14 as shown in FIG. 5. The remainder of the activation front 22 has now passed out of the region of myocardium 10. FIG. 6 shows the region 20, which was initially refractory, beginning to repolarise, whilst the activation front 22 advances towards the region 20. In FIG. 7 the region 20 which was initially refractory has fully repolarised, and the activation front 22 which passed through the fibrous tissue 14 now depolarises the region 20. FIG. 8 shows the activation front 22 leaving the region 20, and depolarising the surrounding myocardium 10, which is no longer refractory. This results in an activation front 22 which is effectively travelling in the opposite direction to that in which it was travelling initially, leading to spiral waves, as indicated by the arrows shown in FIG. 8. As a result, the activation front 22 continues to stimulate muscle tissue 10, causing uncoordinated contractions in the myocardium 10, leading to an arrhythmia, and ventricular fibrillation.

A known way of detecting whether a patient is at risk of VF is to perform a paced electrogram process, by inserting one input electrode and one or more output electrodes into the heart, and applying a pacing signal to the input electrodes.

The output electrodes are typically inserted into the right ventricular septum, the inferior wall of the right ventricle and the right ventricular outflow tract. An electrogram of the potential recorded by the output electrodes is then produced. Electrograms, and other related graphical representations of output signals will also be referred to herein as "electrogram trace" and "trace".

FIG. 9 shows a schematic diagram of a wavefront from a pacing signal passing through homogeneous tissue, in a healthy heart, for example. Two recording electrodes 40, 42 are shown, and the wavefront 44 reaches these in a straightforward manner, giving the electrogram 46 shown, having a single peak, A.

FIG. 10 shows a schematic diagram of a wavefront from a pacing signal passing though diseased tissue 14. As described above with reference to FIGS. 1 to 8, the fibrous tissue 14 causes a slowing of the conduction paths through the diseased region 14. This results in a number of signals being recorded by the recording electrodes 40, 42: in this example, peaks A, B, C, D and E can be seen on an electrogram 60, each peak corresponding to a conduction path having the same letter.

FIG. 11 shows a schematic diagram of pacing sequence 70 which can be used to stimulate at an electrode placed in a region of a patient's heart. As can be seen, the pacing sequence comprises a drive chain S1 with an extrastimulus applied every third beat. This extrastimulus is premature, in that the pacing interval, S1S2 (i.e. the interval between a pulse S1 and a pulse S2) is shorter than the pacing interval S1S1 (i.e. the interval between successive S1 pulses). The pacing interval is also referred to herein as the "coupling interval". In one arrangement the coupling interval S1S2 decreases in 1 ms steps, but the skilled person will appreciate that other coupling intervals are possible, and the shortest period used usually corresponds to the ventricular effective refractory period (VERP). The purpose of applying this stimulus is to stress the heart, to so that effects associated with VF can be displayed. The electrogram produced from this technique is known as an intracardiaelectrogram.

FIG. 12 shows a stimulus produced from a heart, paced with a pulse such as that shown in FIG. 11, the effects of the pulsing being recorded at 3 points in the right ventricle. The S1S1 coupling interval is 490 ms, and the S1S2 coupling interval is 249 ms in this example.

FIG. 13 shows further stimuli produced in a similar way to those in FIG. 12 at each of three recording sites. Furthermore, FIG. 13 shows a comparison between electrograms 80a, 80b, 80c recorded at an S1S2 interval of 350 ms and 250 ms for each of the sites. As can be seen from this Figure, the electrogram traces show an increase in the number of peaks, and an increase in the delay in the signal from the initial pulse 82 (which can be seen on the left hand side of the traces). The interval between the electrograms recorded at 350 and 250 ms differs at each site, showing that the delays are due to activation front passing through the myocardium rather than due to another effect, such as increased stimulus-to-tissue delay (since, if the delay were due to the latter effect, each of the traces would show the same increase in delay).

FIG. 14 shows examples of traces at various S1S2 coupling intervals, showing the differences in traces between a control patient and an HCM patient. Again, as can be seen, the HCM trace shows an increase in the number of peaks, and an increase in the horizontal spread of the trace.

FIG. 15 shows an electrogram 90, with a close up view showing noise in the trace. Each peak of the electrogram is analysed, and can be plotted as a function of the S1S2 coupling interval at which the trace was taken. This is shown in more detail in FIGS. 18 and 19, discussed below.

International patent application having publication number WO94/02201 discusses the use of such graphs in calculating a risk of a patient having myocardial disarray from suffering a VF. Some patients, however, do not exhibit myocardial disarray, but are nevertheless prone to VF and to SCD (such as those patients having long QT syndrome (LQTS)); thus, whilst extremely useful, the techniques described in WO94/02201 are not sufficiently developed for use in identifying all patients at risk from SCD. Various alternative methods have been developed, e.g. on the basis of genotype identification; while certain genotypes of LQTS have been identified, each genotype has a number of different associated phenotypes, meaning that two or more people having the same gene or set of genes associated with LQTS may have hearts displaying different physical characteristics. Further, it seems that different phenotypes have different amounts of risk to VF. As a result, techniques which involve testing the genotype of a patient cannot be used to determine whether an LQTS patient is susceptible to VF.

It is therefore desirable to find a way in which different cardiac conditions, predisposing a patient to VF can be determined from the same experiment and/or the same method of analysis.

It is an object of embodiments of the present invention to provide a system for analyzing electrograms.

SUMMARY OF THE INVENTION

In accordance with a first aspect of the present invention, there is provided a system for use in analysis of electrograms, the system comprising:

a signal generator for generating an input signal;

an input electrode for applying an input signal to a driving region of a heart organ;

an output electrode for receiving an output signal at a driven region of the heart organ, so as to record a value thereof;

a processing system operable to receive signals indicative of said recorded value from the output electrode for analysing conduction paths through the heart organ, wherein the signal generator is operable to generate an input signal comprising a plurality of pulses, at least some of the pulses from said plurality being spaced from each other by a pacing interval;

and wherein the processing system is arranged to identify signal delay between the input signal and the output signal on the basis of the signal received by the output electrode in relation to the plurality of pulses, characterized in that the processing system is arranged to identify a rate of variation in signal delay over a range of values of pacing interval.

Thus, the first aspect of the present invention provides a system adapted for determining a characteristic derivable from an electrogram indicative of a cardiac condition.

The processing system may be arranged to identify first and second rates of variation in signal delay within the range of values of pacing interval, thereby enabling different rates of variation in signal delay to be used in an analysis.

The processing system may be further arranged to compare the first and second rates of variation in signal delay so as to generate a parameter having a value indicative of a difference in said first and second rates of variation in signal delay, thereby allowing the different rates of variation in signal delay to be quantified.

The processing system may be further arranged to compare said parameter with at least one known parameter value, so as to identify one of a plurality of physiological cardiac conditions.

The processing system may be arranged to use the output signal so as to construct a graphical representation of output potential against the pacing interval. With such arrangements the first and second rates of variation in signal delay typically relate to said graphical representation. More specifically, the first and second rates of signal delay may relate to the gradient of a first portion of the graphical representation, and the gradient of a second portion of the graphical representation, respectively.

The parameter may be derived from a relative angle between the gradient of the first portion of the graphical representation, and the gradient of the second portion of the graphical representation. If the parameter value is lower than 150° a first physiological cardiac condition, such as long QT syndrome, may be identified and, if said parameter value is higher than approximately 150°, a second physiological cardiac condition, such as hypertropic cardiomyopathy, may be identified. These respective conditions can be associated with ranges of the parameter values: for example, if the parameter value is between approximately 115° and 135° the first physiological cardiac condition may be identified and, if the parameter value is between approximately 155° and 170°, the second physiological cardiac condition may be identified.

The processing system may be further arranged to compare said parameter value with an average parameter value, and, if said parameter value is lower than said average parameter value, the first physiological cardiac condition can be identified; however, if the parameter value is higher than said average parameter, the second physiological cardiac condition is identified.

The processing system may be arranged to identify a rate of variation in signal delay over a range of values of pacing interval for a plurality of heart organs, and wherein said processing system may be further adapted for:

deriving a respective said parameter value for said plurality of heart organs, to give a plurality of parameter values;

defining an average of said plurality of parameter values, to give an average parameter value; and comparing said average parameter value to a parameter value from a heart organ, wherein, if said parameter value is lower than said average parameter value, a first physiological cardiac condition is identified and, if said parameter value is higher than said average parameter value, a second physiological cardiac condition is identified.

This allows a cardiac condition to be identified in a population of patients, and further, it allows the probability that a patient has a cardiac condition to be determined, relative to the population sampled.

The first physiological cardiac condition may be long QT syndrome and the second physiological cardiac condition may be hypertropic cardiomyopathy.

In accordance with a second aspect of the present invention, there is provided a system for use in analysis of electrograms, the system comprising:

a signal generator for generating an input signal;

an input electrode for applying an input signal to a driving region of a heart organ;

an output electrode for receiving an output signal at a driven region of the heart organ, so as to record a value thereof;

a processing system operable to receive signals indicative of said recorded value from the output electrode for analysing conduction paths through the heart organ, wherein the signal generator is operable to generate an input signal comprising a plurality of pulses, at least some of the pulses from said plurality being spaced from each other by a pacing interval;

and wherein the processing system is arranged to identify signal delay between the input signal and the output signal on the basis of the signal received by the output electrode in relation to the plurality of pulses, characterized in that the processing system is arranged to:

characterized in that the processing system is arranged to:

process the output signal by correlating the output signal with a first template to produce a first correlated trace;

process the output signal by correlating the output signal with a second template to produce a second correlated trace; and compare said first correlated trace with said second correlated trace, so as to produce an output indicative of similarities in said first and second correlated traces.

Thus, the invention in this aspect relates to a system in which an electrogram can be filtered using at least two templates, and is advantageously used to remove noise from a signal.

In accordance with a third aspect of the present invention, there is provided a system for use in analysis of electrograms, the system comprising:

a signal generator for generating an input signal;

an input electrode for applying an input signal to a driving region of a heart organ;

an output electrode for receiving an output signal at a driven region of the heart organ, so as to record a value thereof;

a processing system operable to receive signals indicative of said recorded value from the output electrode for analysing conduction paths through the heart organ, wherein the signal generator is operable to generate an input signal comprising a plurality of pulses, at least some of the pulses from said plurality being spaced from each other by a pacing interval;

and wherein the processing system is arranged to identify signal delay between the input signal and the output signal on the basis of the signal received by the output electrode in relation to the plurality of pulses, characterized in that the pacing interval between a first pulse of said plurality a second pulse of said plurality is arranged to increase from a first value $t_1$ to a second value $t_2$.

Thus, the invention in the third aspect provides a system which can perform an electrogram process which reduces the effect of altering the blood flow to the heart. In some arrangements $t_1$ may be less than approximately 350 ms and $t_2$ may be greater than approximately 350 ms.

In accordance with a fourth aspect of the present invention, there is provided a system for use in analysis of electrograms, the system comprising:

a signal generator for generating an input signal;

an input electrode for applying an input signal to a driving region of a heart organ;

an output electrode for receiving an output signal at a driven region of the heart organ, so as to record a value thereof;

a processing system operable to receive signals indicative of said recorded value from the output electrode for analysing conduction paths through the heart organ, wherein the signal generator is operable to generate an input signal comprising a plurality of pulses, at least a first set of pulses from said plurality being spaced from each other by a first pacing interval;

and wherein the processing system is arranged to identify signal delay between the input signal and the output signal on the basis of the signal received by the output electrode in relation to the plurality of pulses, characterized in that the plurality of pulses further comprises a second set of pulses, spaced from each other by a second pacing interval, and a third set of pulses, spaced from each other by a third pacing interval.

Thus, the system in the fourth aspect provides a system which can perform an electrogram process which puts the heart under greater stress than in known electrograms, so that effects associated with VF can be provoked.

Further, because a greater number of data are generated, the system in this aspect allows greater scope for analysis of the electrograms produced. In terms of pacing intervals, any one, or a combination of, the following can be used: the first pacing interval may be a constant value; the second pacing interval may be a constant value; the second pacing interval may vary; the third pacing interval may be a constant value; the third pacing interval may vary; the second pacing interval may be shorter than said first pacing interval; and/or the third pacing interval may be shorter than said first pacing interval.

The processing system may be arranged to identify a rate of variation in signal delay over a range of values of second pacing interval and third pacing interval so as identify a rate of variation in signal delay over a range of values of second pacing interval and third pacing interval.

The processing system may be further arranged to derive first and second rates of variation in signal delay within the range, and to compare the first and second rates of signal delay so as to generate a function indicative of said variation in signal delay over a range of values of second pacing interval and third pacing interval.

The processing system may be further arranged to use the output signal so as to construct a graphical representation of recorded output potential against the second pacing interval and third pacing interval; in view of the fact there are two pacing intervals, the graphical representation preferably comprises a surface, and said first and second rates of variation in signal delay relate to said graphical representation.

The first and second rates of variation in signal delay may relate to a first plane, positioned parallel to a plane normal to the surface of a first portion of the graphical representation, and a second plane, positioned parallel to a plane normal to the surface of the second portion of the graphical representation, respectively.

The function may be derived from a line of intersection between said first plane and said second plane.

The processing system is further arranged to compare said function with a range of known functions, to identify one of a plurality of physiological cardiac conditions.

The system may comprise at least four output electrodes for receiving an output signal at a respective plurality of driven regions of the heart organ.

In accordance with a fifth aspect of the present invention, there is provided a system in use in analysis of electrograms, the system comprising:

a signal generator generating an input signal;

an input electrode applying an input signal to a driving region of a heart organ;

an output electrode receiving an output signal at a driven region of the heart organ, so as to record a value thereof;

a processing system operable to receive signals indicative of said recorded value from the output electrode for analysing conduction paths through the heart organ, wherein the signal generator is operable to generate an input signal comprising a plurality of pulses, at least some of the pulses from said plurality being spaced from each other by a pacing interval;

and wherein the processing system is arranged to identify signal delay between the input signal and the output signal on the basis of the signal received by the output electrode in relation to the plurality of pulses, characterized in that at least one of said driving region or driven region of the heart corresponds to a localized position of myocardial disarray.

Thus, the invention in this aspect provides a system which can produce an electrogram indicative of damage in a post-coronary patient, and can analyse the results thereof.

In accordance with a sixth aspect of the present invention, there is provided a system in use in analysis of electrograms, the system comprising:

a plurality of electrodes, each disposed within a region of a heart organ, a first of the plurality being disposed in a first region and being responsive to an input signal so as to stimulate a muscle of the heart, and a second of the plurality being disposed in a second region, different to the first region, and being responsive to a signal received within the second region so as to record a value thereof;

a processing system operable to receive signals indicative of said recorded value from the second electrode so as to analyse conduction paths through the region of the heart organ, wherein the input signal comprises a sequence of pulses, the sequence comprising a first set of pulses and a second set of pulses, a given pulse within the first set being spaced from a next pulse in the first set by a constant interval, and individual pulses within the second set being spaced from respective individual pulses within the first set by a pacing interval, and wherein the processing system is arranged to identify signal delay on the basis of the signal received by the second electrode in relation to the sequence of pulses, characterized in that the processing system is arranged to identify variation in signal delay over a range of values of pacing interval so as to derive first and second signal delay characteristics within the range, and to compare the first and second signal delay characteristics so as to generate a parameter indicative of said variation in signal delay.

In accordance with a seventh aspect of the present invention, there is provided apparatus for identifying cardiac electro-physiological behaviour by analysis of paced cardiac electrograms, in which a pulsed signal having a pacing interval between at least some of the pulses in said signal, is passed through the heart of a patient, the apparatus comprising processing means, wherein said processing means being arranged for:

constructing a graphical representation from values of delay in said pulsed signal passing through the heart of the patient as a function of said pacing interval;

defining a first portion and a second portion for said graphical representation;

determining a first parameter for said first portion of the graphical representation, based on a characteristic of said first portion of the graphical representation, determining a second parameter for said second portion of the graphical representation, based on a characteristic of said second portion of the graphical representation, comparing said first parameter with said second parameter to obtain a third parameter; and outputting data indicative of a physiologically-significant feature from a set of at least two physiological cardiac conditions depending on the value of said third parameter.

Further features and advantages of the invention will become apparent from the following description of preferred embodiments of the invention, given by way of example only, which is made with reference to the accompanying drawings.

BRIEF DESCRIPTION OF THE DRAWINGS

FIG. 17b shows electrogram traces processed in accordance with the techniques shown in FIG. 17a;

FIG. 17c shows electrogram traces processed in accordance with the techniques shown in FIG. 17a;

DETAILED DESCRIPTION OF THE INVENTION

Figure 1:
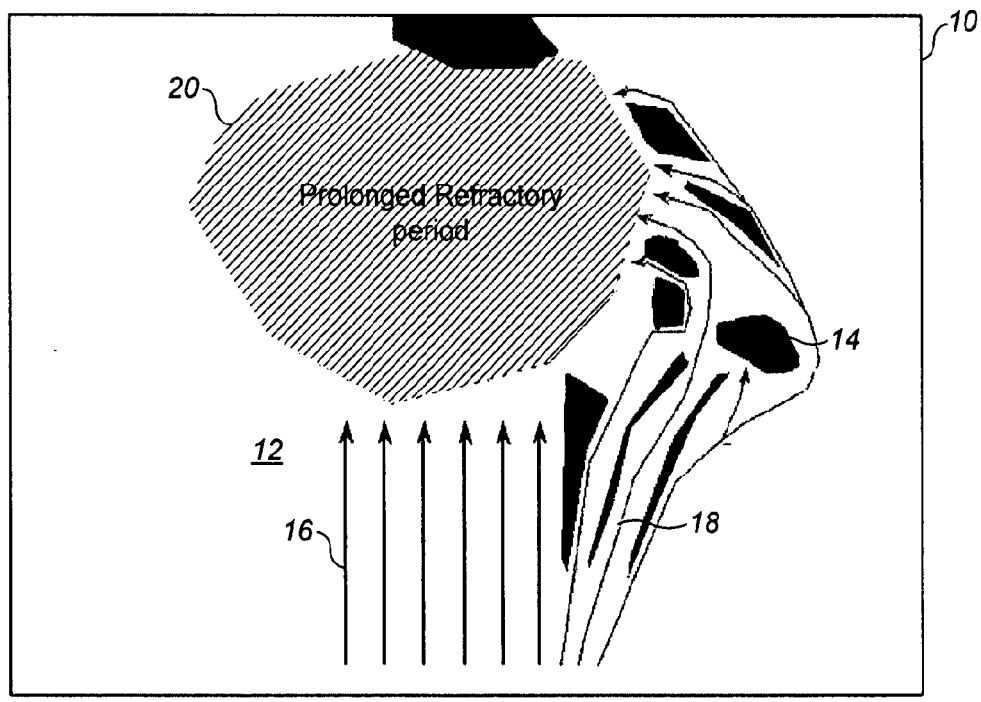
FIG. 1 is a schematic diagram showing a first stage of conduction through myocardium.
Figure 2:
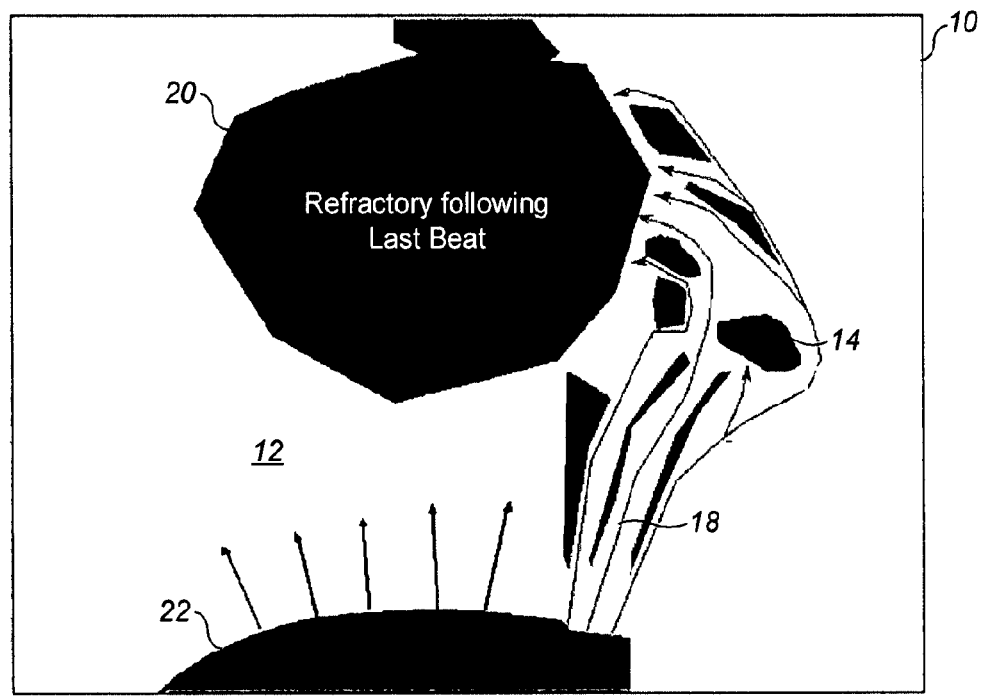
FIG. 2 is a schematic diagram showing a second stage of conduction through myocardium.
Figure 3:
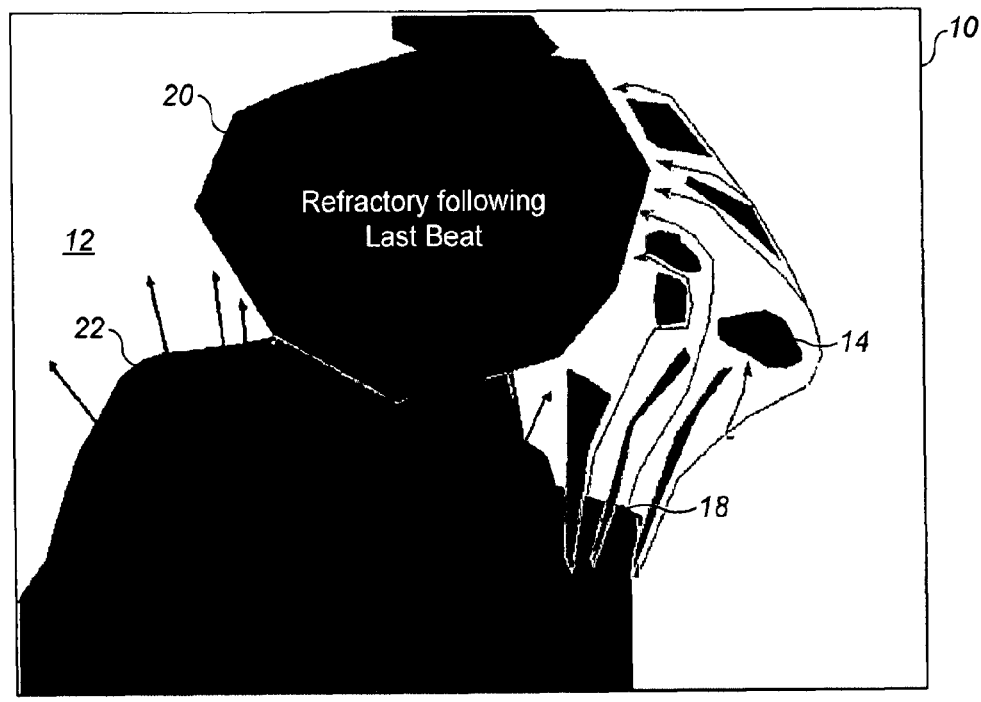
FIG. 3 is a schematic diagram showing a third stage of conduction through myocardium.
Figure 4:
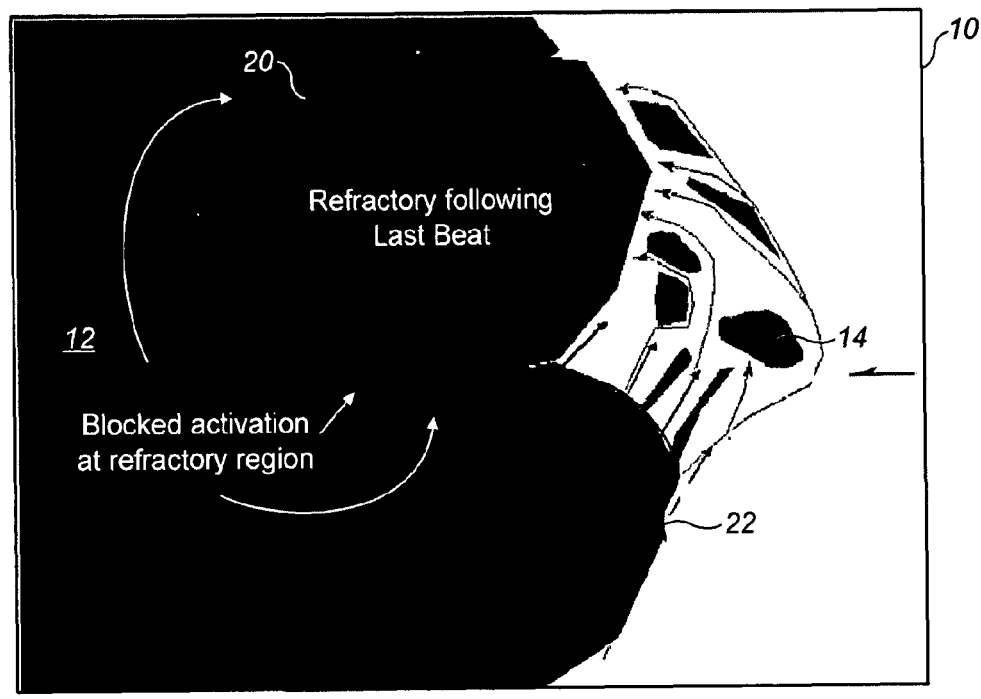
FIG. 4 is a schematic diagram showing a fourth stage of conduction through myocardium.
Figure 5:
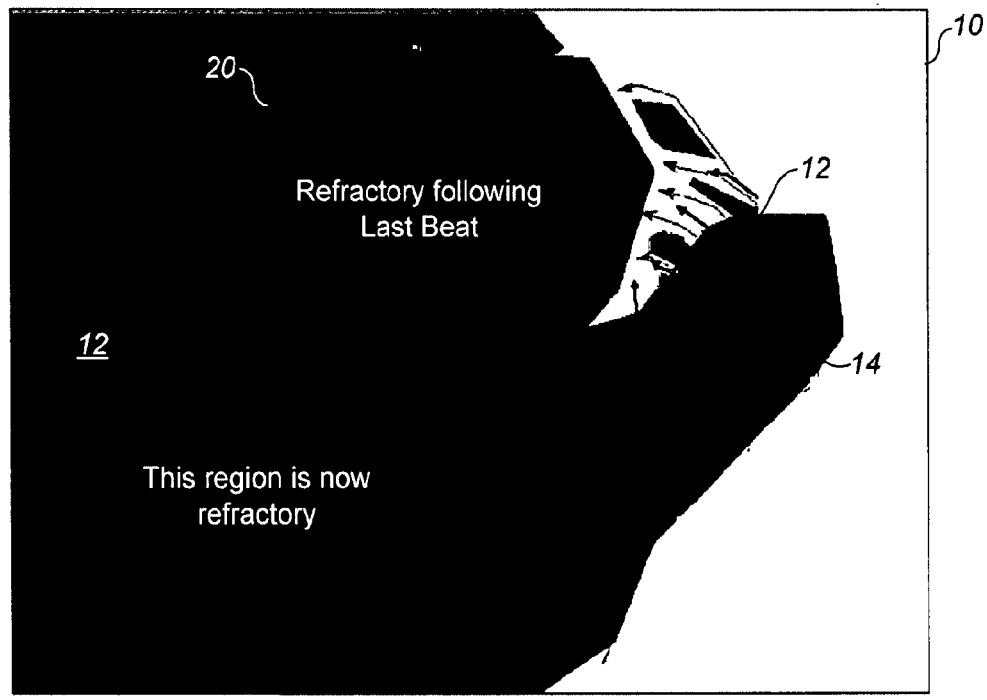
FIG. 5 is a schematic diagram showing a fifth stage of conduction through myocardium.
Figure 6:
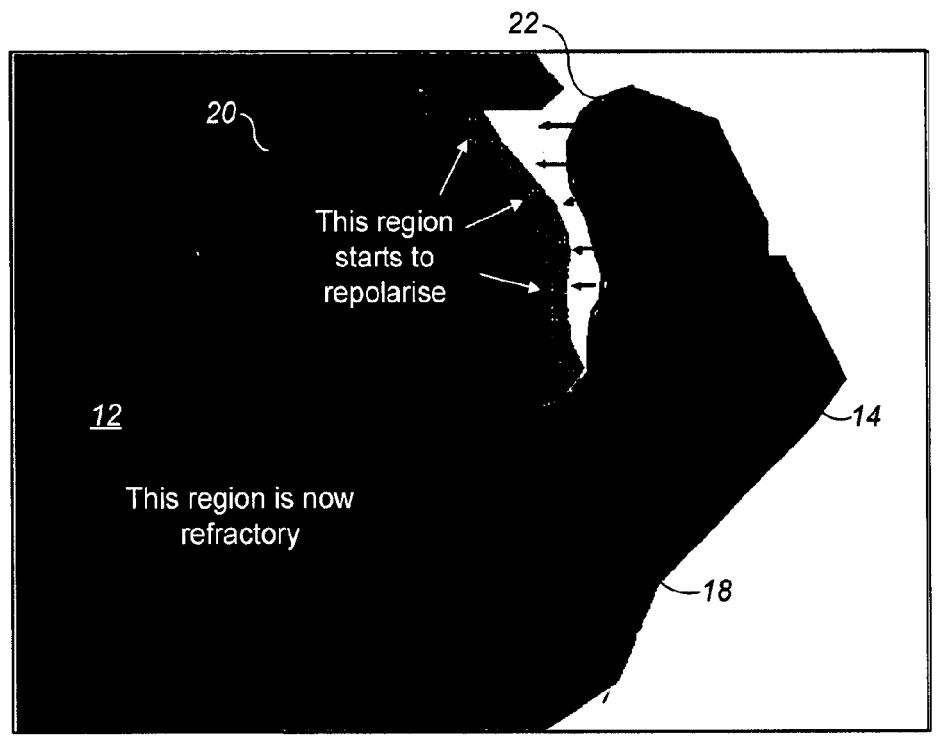
FIG. 6 is a schematic diagram showing a sixth stage of conduction through myocardium.
Figure 7:
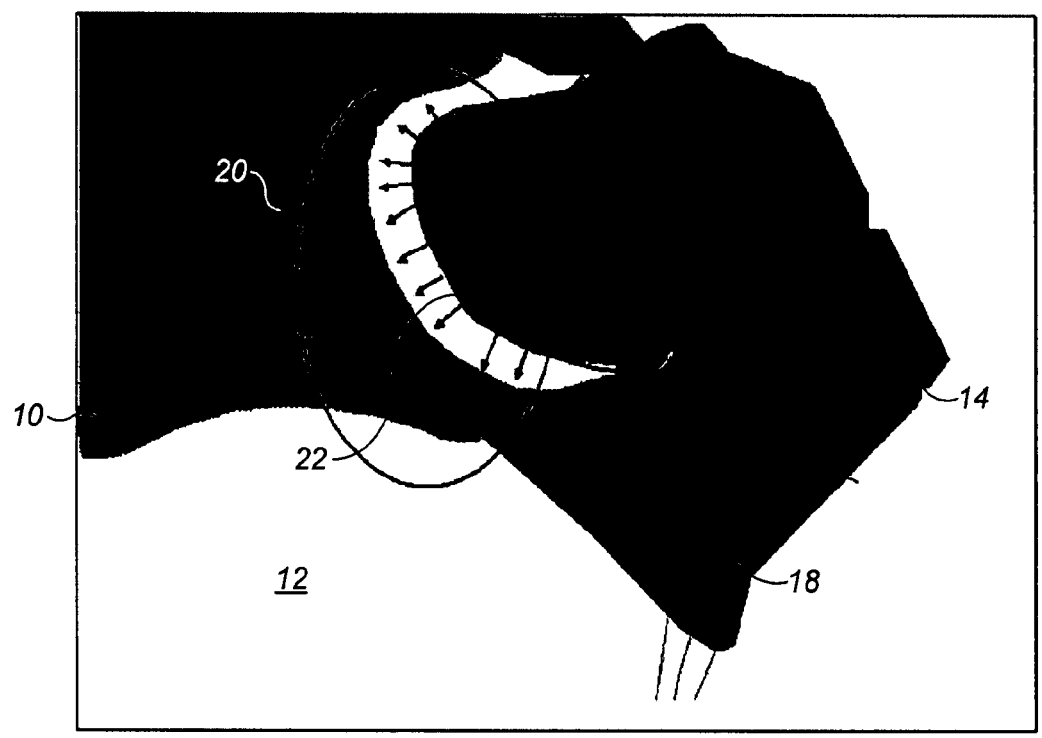
FIG. 7 is a schematic diagram showing a seventh stage of conduction through myocardium.
Figure 8:
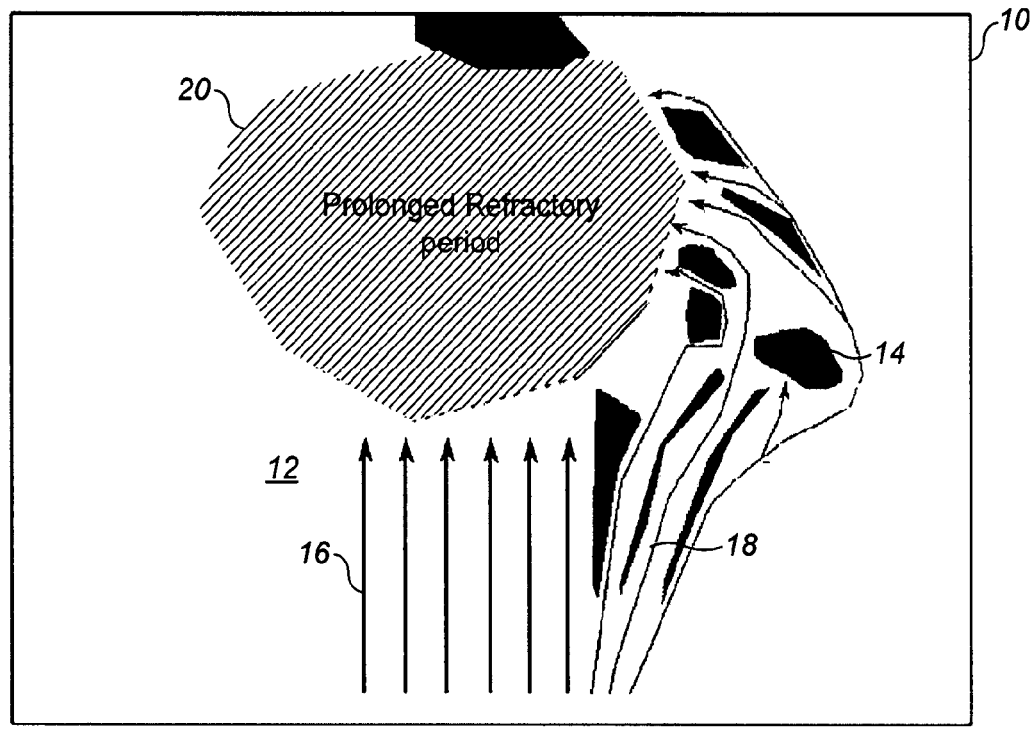
FIG. 8 is a schematic diagram showing an eighth stage of conduction through myocardium.
Figure 9:
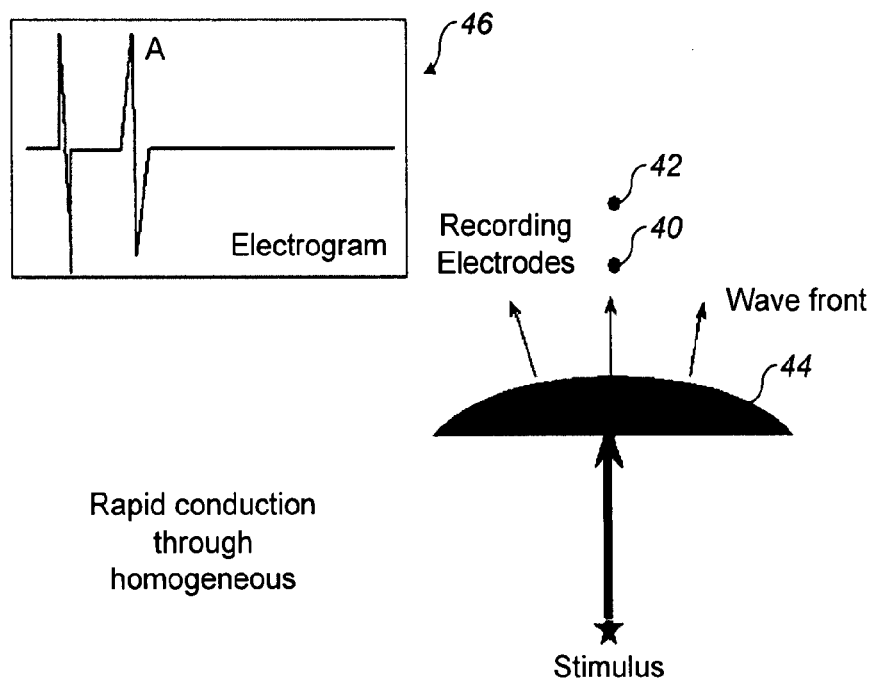
FIG. 9 is a schematic diagram showing a conduction wavefront.
Figure 10:
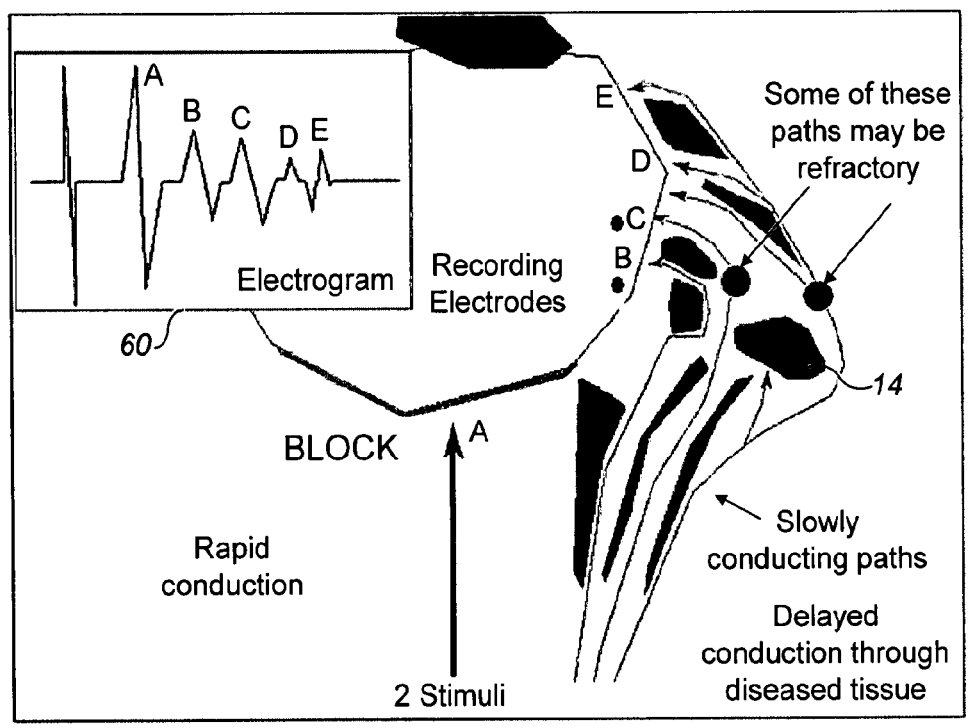
FIG. 10 is a schematic diagram showing sites at which recording electrodes are placed in the myocardium.
Figure 11:
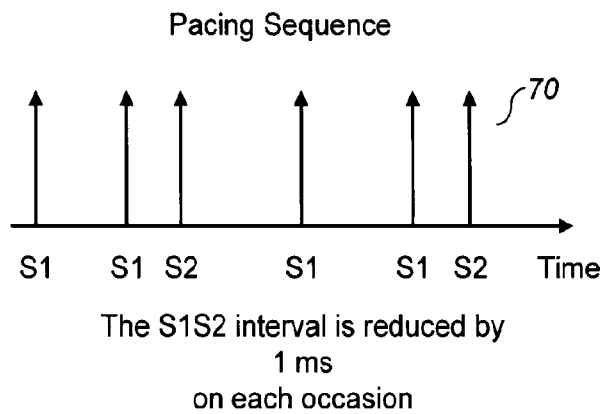
FIG. 11 is a schematic diagram showing sites at which recording electrodes are placed in the heart, together with a schematic diagram showing the pacing sequence.
Figure 12:
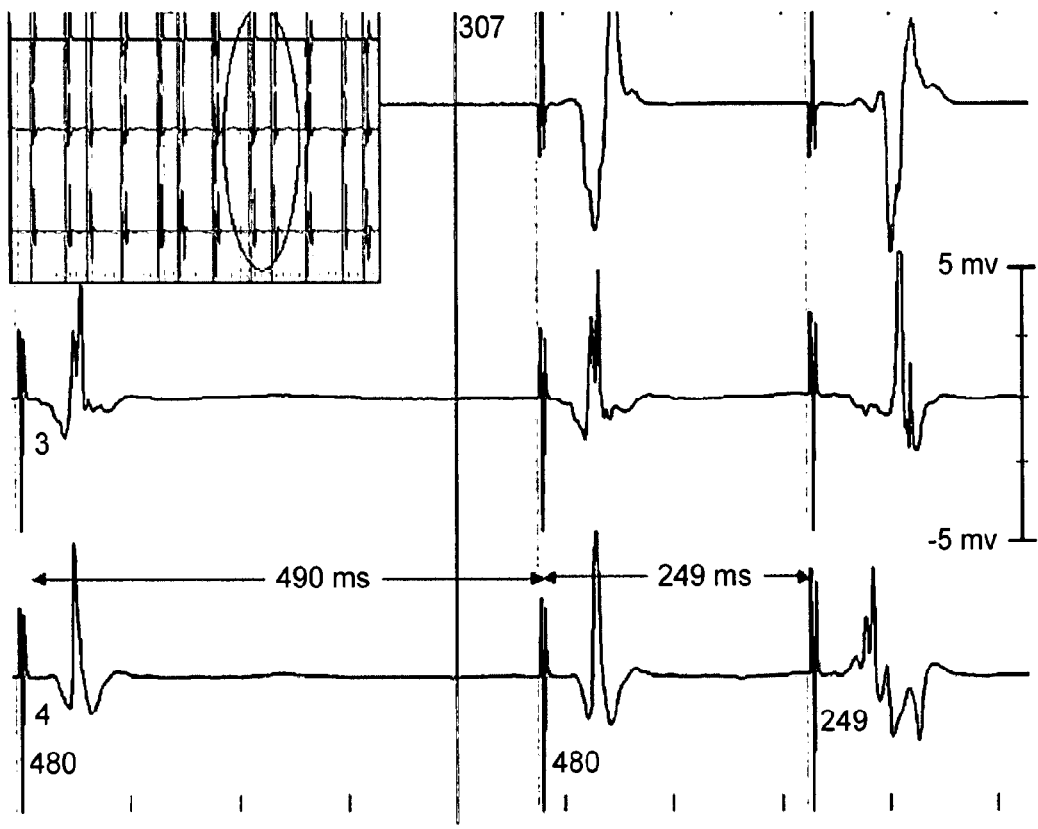
FIG. 12 shows an electrogram trace produced by pacing the heart.
Figure 13:
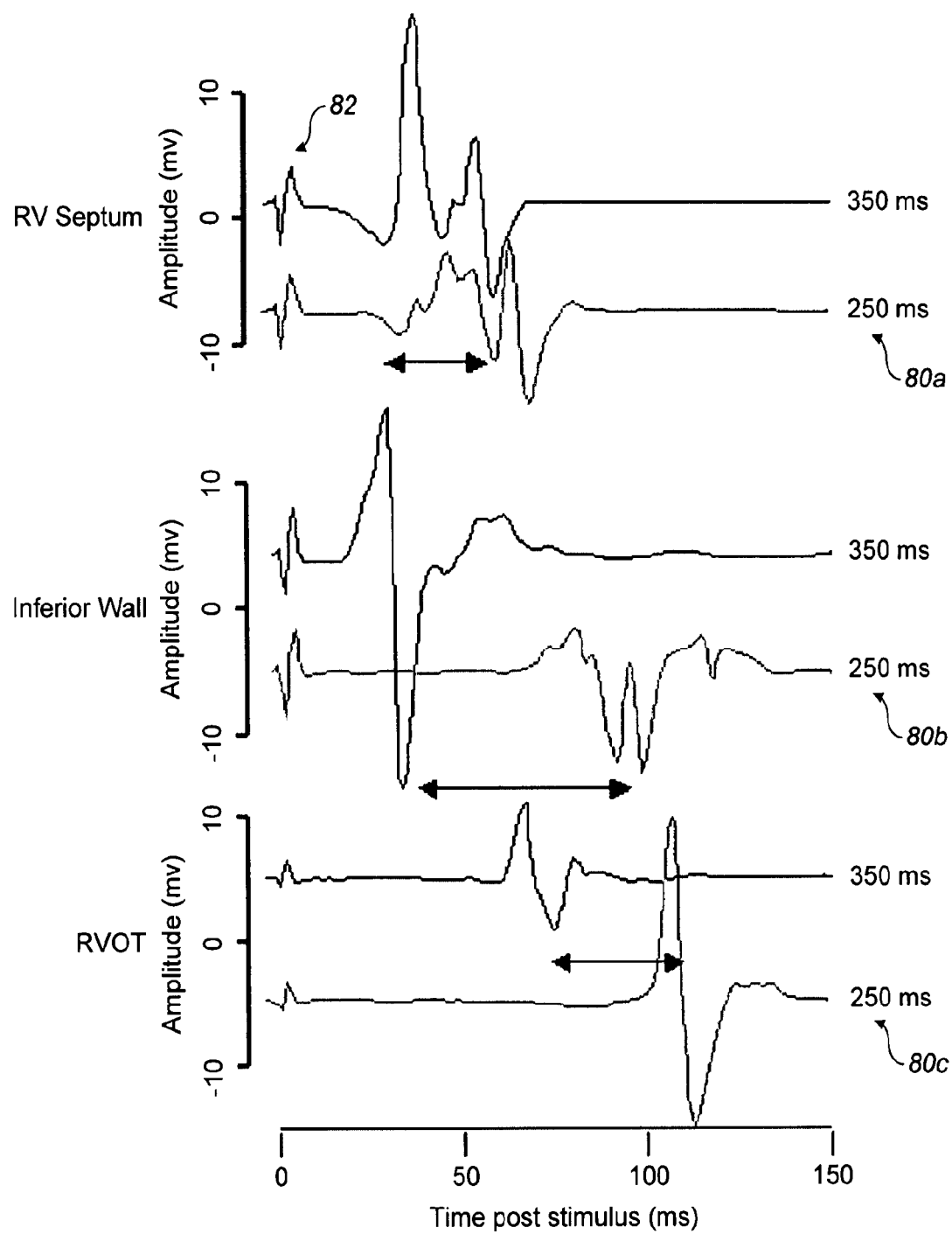
FIG. 13 shows examples of an electrogram trace at different pacing intervals.
Figure 14:
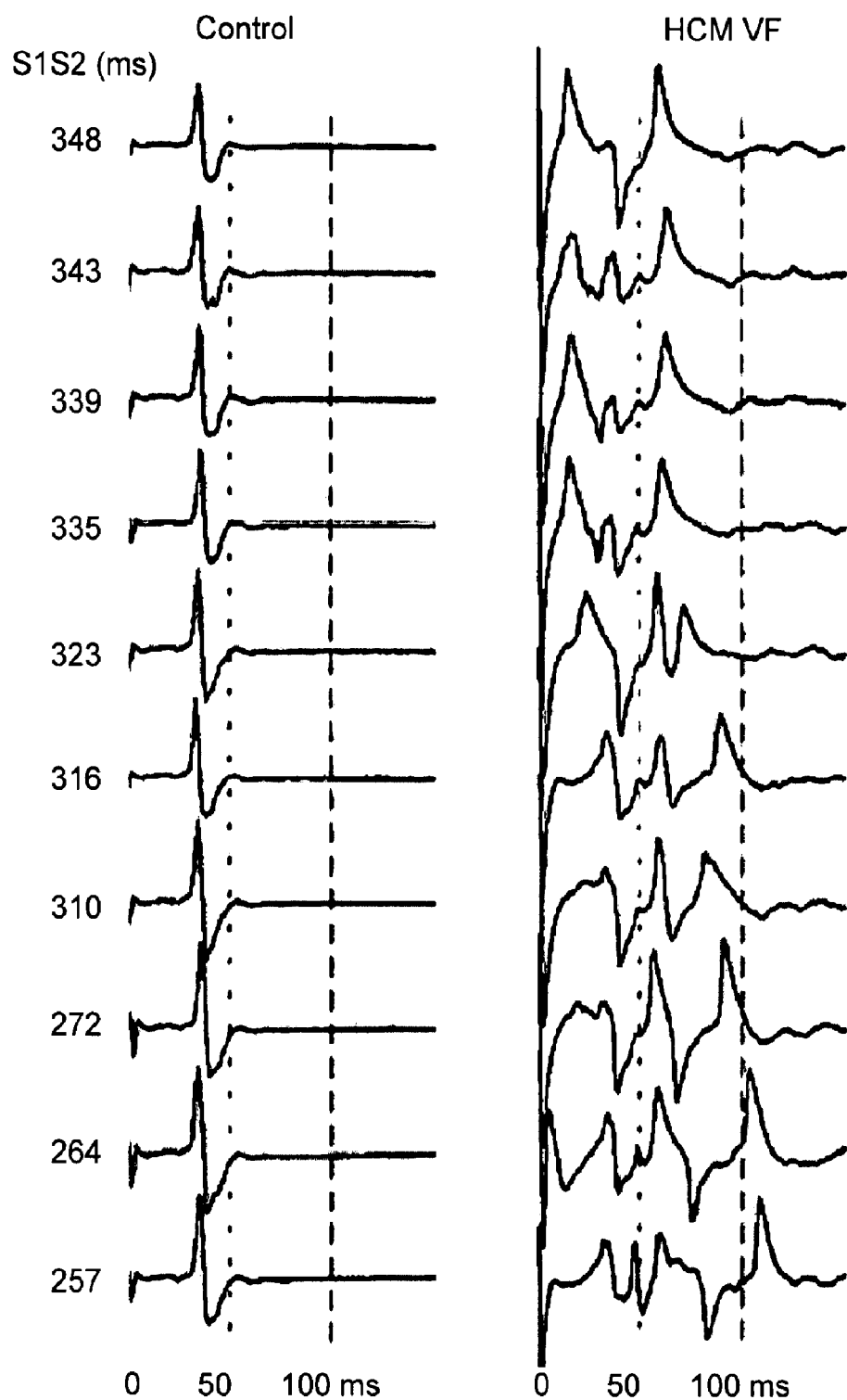
FIG. 14 shows examples of electrogram traces at different pacing intervals for control patients and from VF patients.
Figure 15:
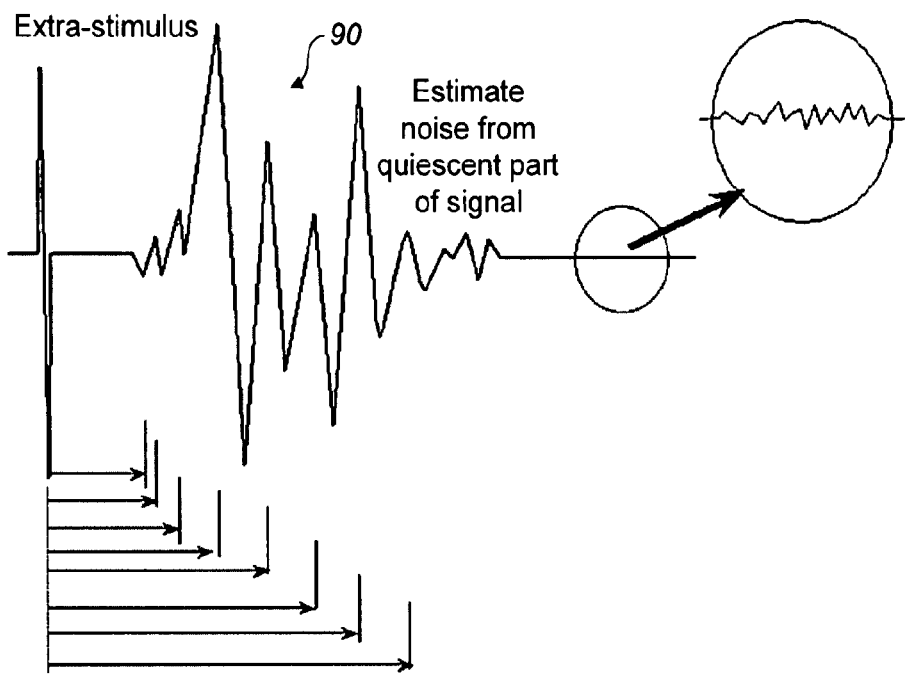
FIG. 15 shows an example of an electrogram trace.

As discussed above, the present invention relates to the apparatus for performing and analysing paced electrograms. The present invention includes various methods and arrangements each of which will be discussed in detail in turn.
Processing of Data from Electrograms Aspects of the processing of an electrogram 100 produced from stimulating a heart by inserting electrodes therein, for example, as described with reference to FIGS. 9 to 11 will firstly be described. An aspect of particular importance to the interpretation of electrograms is the post-processing of signals so as to reduce noise, so that potentials may be distinguished from noise in the signal, and so that the potentials can be recorded accurately. As is known in the art, signals inherently contain a mixture of noise and data, the noise originating from background sources such as fluorescent lights, X-ray heads, motors, monitors, other equipment commonly found in labs or hospitals, or poor catheter connections. Reducing noise from a signal can be crucial, particularly in cases where a noisy signal has similar characteristics to a data signal; in the case of electrograms, it is particularly important to identify and filter out erroneous peaks, which may produce false results when the electrogram 100 is analysed.

In a first arrangement a series of templates is used to filter out the noise from an electrogram, as will be described with reference to FIGS. 16 and 17a to 17e.

Figure 16:
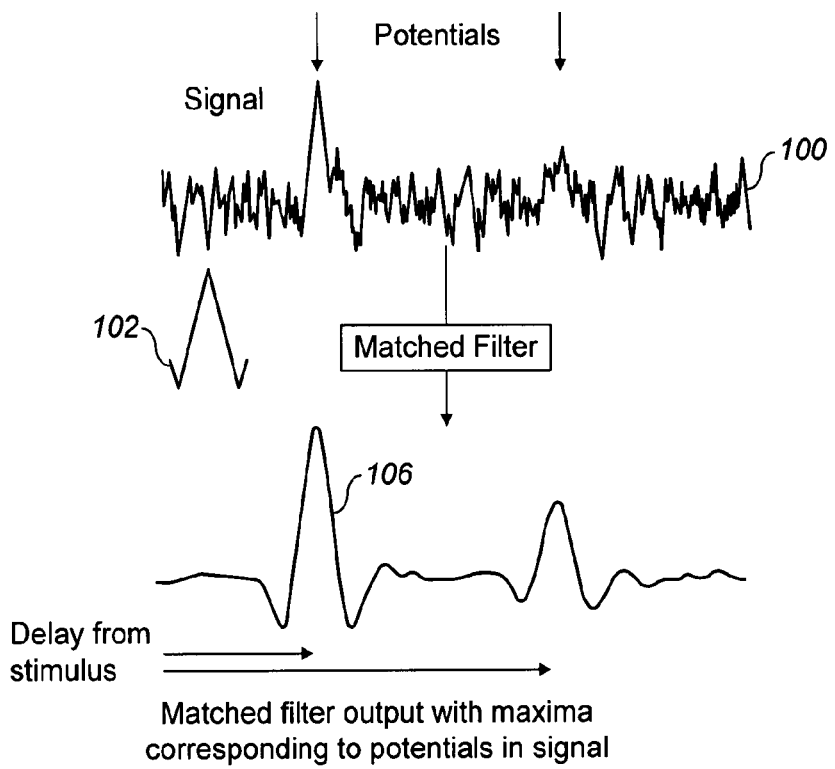
FIG. 16 shows an example of how an electrogram trace is processed.
Figure 17A:
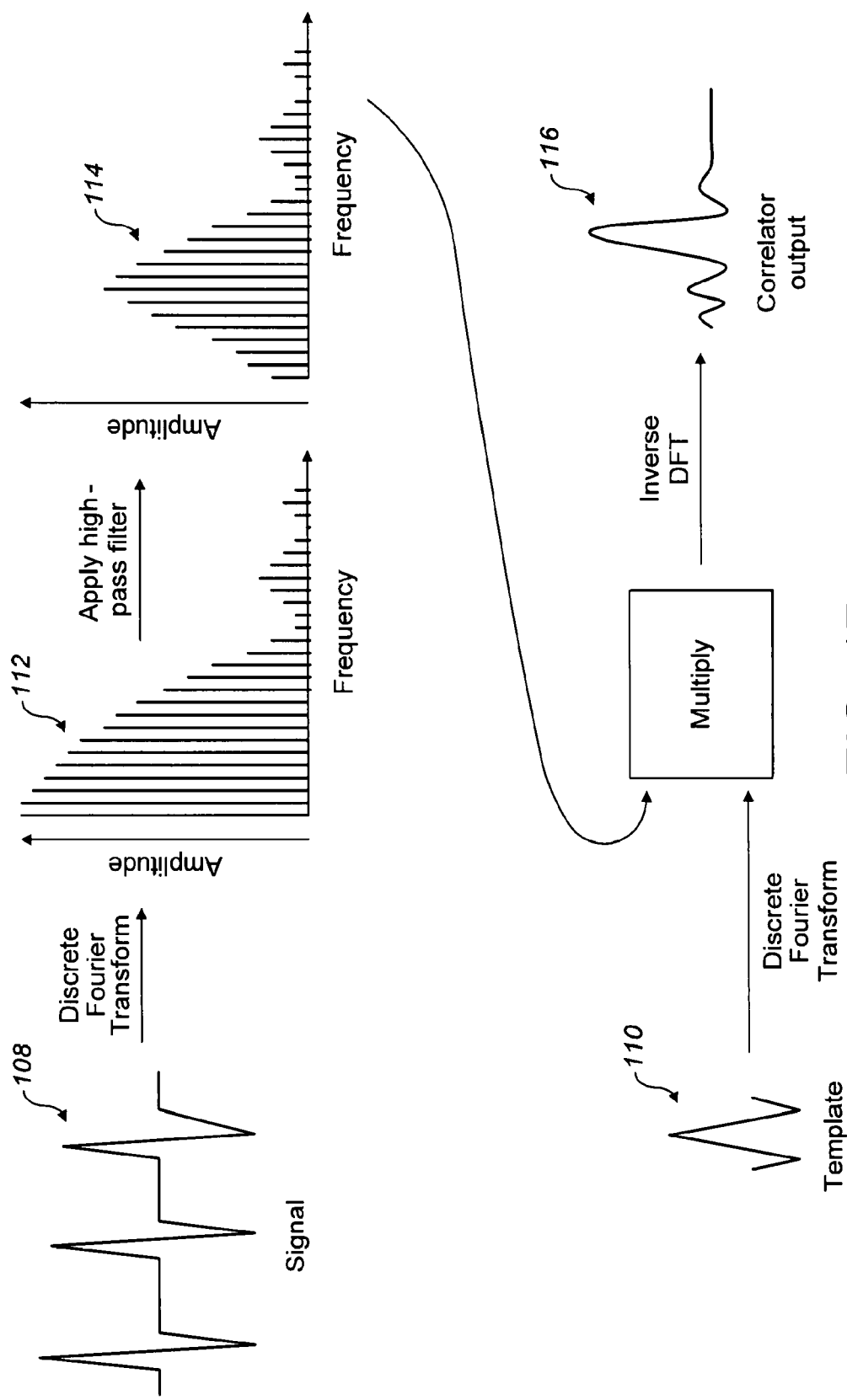
FIG. 17a is a schematic diagram showing the methods used in the processing of an electrogram trace in more detail.

FIG. 16 shows a single template 102 which may be correlated to a noisy simulated electrogram trace 100, together with the simulated electrogram 106 after it has been filtered with the template. FIG. 17a shows the processing of an output signal 108 with a template 110. The frequency components of the signal 108 (in the time domain) are first ascertained by applying a discrete fourier transform (DFT) (or fast fourier transform equivalent) to the signal 108. This can be shown as a representation 112 of the signal in the frequency domain after the transformation, where the discrete frequency components can be seen. A high-pass filter is then applied to the frequency components, which has the effect of truncating the lower frequency components (such as those below 150 Hz, which may be generated by hospital or laboratory equipment, for example) whilst leaving the high frequency components (the abscissa of the representation has been shifted from that of the representation after the DFT) present in the signal 114.

The template 110 to be compared with the signal 108 is then modified by means of a DFT. The discrete frequency components of the template are then compared to those of the signal (after filtering) 114, and an inverse DFT is applied, to produce a correlator output 116 for that template. As an alternative to correlating signals 114 and the frequency components of the template, the signal and the template could be convolved. This process can be repeated for a number of templates.

Figure 17B:
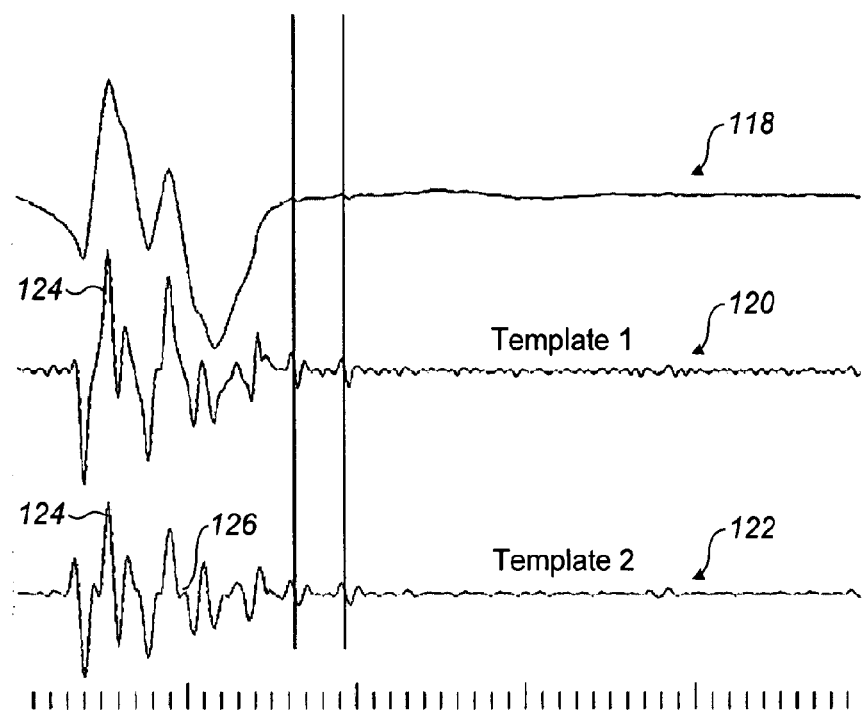

FIG. 17b shows an electrogram 118, together with two examples (120, 122, each referred to as a "trace") of the electrogram 118 after it has been correlated with a template. A first correlated trace 120 has been correlated with template 1, while a second correlated trace 122 has been correlated with template 2. It should be noted that the scale on the ordinate is different for the three traces shown in FIG. 17b. As can be seen from the first and second correlated traces, as a result of processing with the respective templates there are some peaks 124 common to both outputs, and some 126 different to both outputs.

Figure 17C:
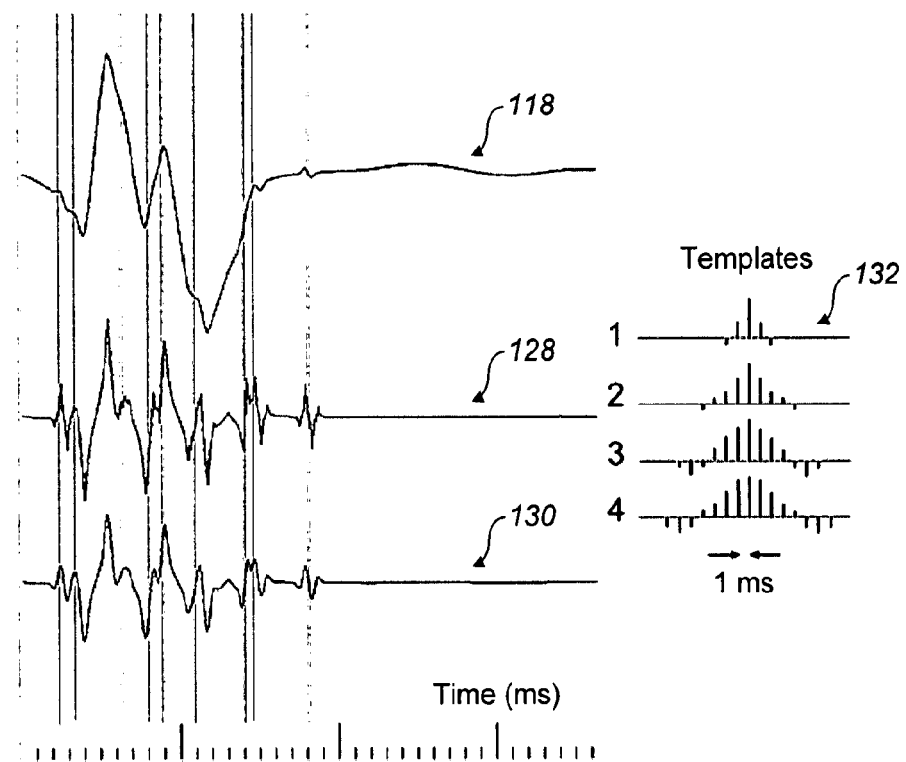

FIG. 17c shows a trace 128 derived from the electrogram 118 by high pass filtering the electrogram 118, and further shows a trace 130 produced by correlating the electrogram 118 with a template, such as template 2. FIG. 17c further shows schematic representations of a series of 4 different templates 132.

Figure 17D:
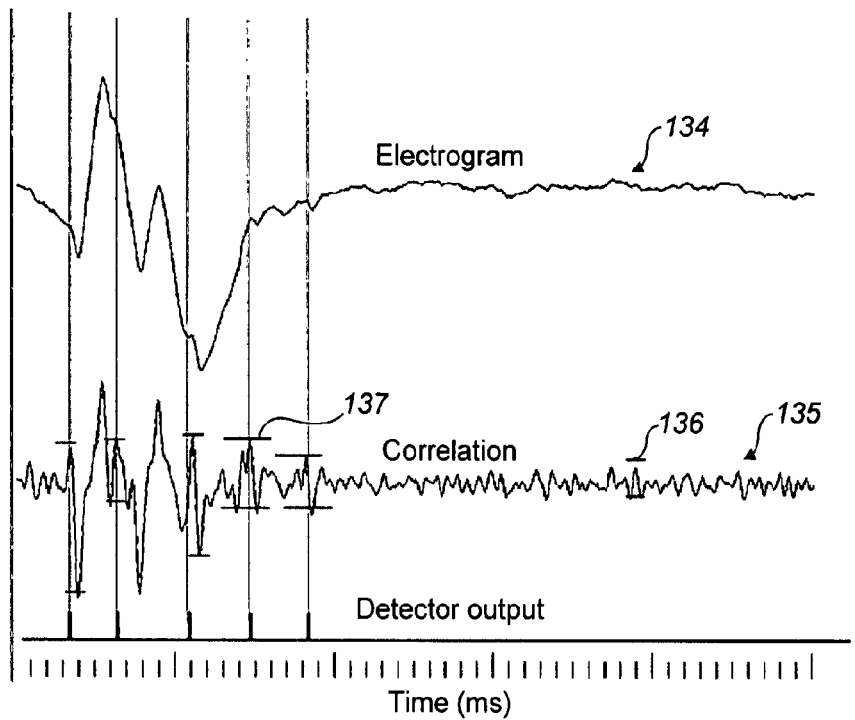
FIG. 17d shows a further step in the processing of electrogram traces.

The noise in a trace, such as an electrogram representing raw data, or such as a correlated trace produced by correlating an electrogram with a template, as described above can be further reduced by a second method, shown in FIG. 17d. FIG. 17d shows an electrogram 134, and a correlated trace 135 derived from this electrogram (by correlation with a template, as discussed above, for example). The peak to peak amplitude 136 of the correlated trace 135 in the range 200 ms to 400 ms is analysed, and any potentials having an amplitude below this are categorised as noise. In this way, the parameter of maximum peak to peak value is effectively used as an amplitude threshold for peaks which may be caused by data, i.e. any peak having an amplitude below this threshold is considered to be noise, and any peak having an amplitude above this threshold is analysed, as it may be caused by data. In terms of a value for this threshold, an amplitude value of approximately 5 µV has been found to be suitable.

This threshold amplitude is then applied to the trace in the range 10 ms and 200 ms (which is the part of the trace which is typically analysed, using the techniques described herein, for example). In this case, any peaks having a lower amplitude than this threshold are discarded, and the peaks 137 having amplitudes greater than the threshold are retained for analysis.

Thus, in the example described above, four templates are used remove parts of the electrograms which do not fit with the template, and produce a correlated trace corresponding to each template. The correlated trace is then processed as shown in FIG. 17d to further reduce the amount of noise in the trace, and since this method is essentially accept/reject based on the amplitude, a binary method of reducing noise is used.

The resultant correlated traces may be used in a number of different ways. For example traces having high correlation values (i.e. one or more peaks in the resultant correlated trace have a correlation of 1 or approaching 1) can be used as the corrected trace, on which the electrogram analysis is subsequently based. Alternatively, the correlation values associated with different templates can be compared with each other, so as to obtain an average. Alternatively, two or more of the correlated traces may be processed with an "and" operator, to remove solitary peaks, or and "or" operator, together with a threshold value can be used, to show peaks above a threshold value which have been picked up by one template.

Figure 17E:
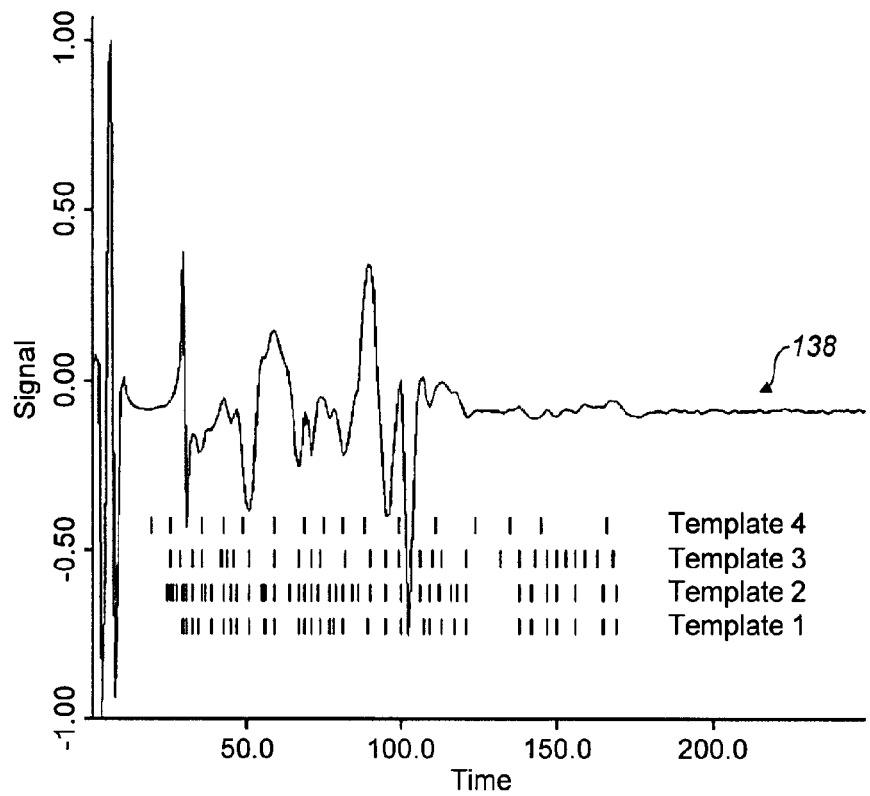
FIG. 17e shows an electrogram trace, and the results of processing the electrogram trace.

It has been found that having a series of templates to filter different electrograms is sufficient to filter electrograms from the majority of patients. For example, a series of four templates may be used. These templates may be defined on the basis that they resemble data in a typical electrogram, and they may be time-dilated versions of each other. For example the series may comprise a master template (template 1), which is shorter than the others, meaning that template 1 will typically pick up most of the data in the electrogram, together with some noise. The other templates are of varying lengths, and the longest of these will typically pick up less data (i.e. it may miss small electrogram peaks caused by data), but will also pick up less noise. FIG. 17e shows an electrogram 138, together with a representation of the peaks determined by using the binary noise reduction techniques described above for each of the templates.

Preferably, the templates are used as follows: an electrogram is correlated with template 1, and a correlated output trace is produced. This correlated output trace is then further analysed using the accept/reject threshold method discussed above. These steps are then repeated with the other three templates, to produce three other output traces, corresponding to the respective output traces from templates 2, 3 and 4. The output trace from template 1 is then compared to the traces produced from the other templates 2, 3 and 4. The output trace produced from one of templates 2, 3 and 4 having the highest number of peaks in common with those produced with template 1 (or otherwise showing the best match with the output trace produced with template 1) is then selected for each electrogram. This selected output trace is compared with template 1, by using an "and" operator, for example, as discussed above.

The same four templates can be used for electrograms produced from different patients. For example, an electrogram from patient 1 is processed with templates 1-4, in the manner described above. The output trace from template 1 is then compared with the output traces from the other templates. In this example, the correlated output trace from template 4 is selected on the basis that it is the best match to the output trace from template 1. Thus, the outputs from template 1 and template 4 are compared for patient 1, and the corrected trace output from this comparison is used for analysis of data collected from patient 1. In a further example, the output trace from template 2 best matches the output trace from template 1 for patient 2. Therefore these output traces are compared for patient 2. Thus, the series of 4 templates can be used to tailor the noise reduction in electrograms for a variety of patients.

Considering again the step of high-pass filtering the DFT signal 112, filtering an electrogram in this manner may be used to determine abnormalities in the conduction substrate of the heart muscle, since if a signal passing through myocardium is subject to delayed conduction (as discussed above) a small, distinct activation wavefront may be incident on an output electrode, causing a small peak in the electrogram. This peak may be superimposed on part of a larger peak, or in another area having high gradient, so it may be difficult to see. If the electrogram having such a small peak is filtered with a high-pass filter these small peaks will become more noticeable. Since the peaks are indicative of a delayed conduction through myocardium, analysis of these peaks may be used to determine information about the conduction paths and/or discontinuous conduction paths through the myocardium.

Method of Analyzing Paced Electrograms

Figure 18:
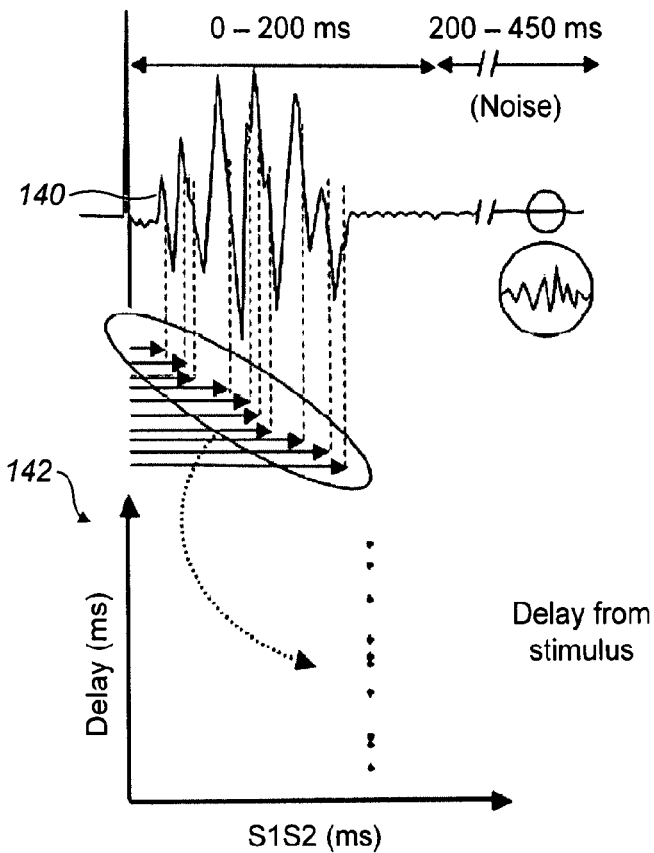
FIG. 18 shows an example of how the electrogram trace is used to plot a conduction curve.

Aspects of analyzing a paced electrogram in order to determine a cardiac condition will now be described with reference to FIG. 18.

As mentioned above, each of the peaks of an electrogram 140 can be plotted on a graph 142 according to their delay from a given pacing signal. This is shown in FIG. 18 for a given electrogram, where dotted lines show the delay having been determined for each of the peaks. Each of these peaks is represented as points on the graph 142, the points having an x co-ordinate according to the S1S2 coupling interval at which the electrogram 140 was taken.

Figure 19:
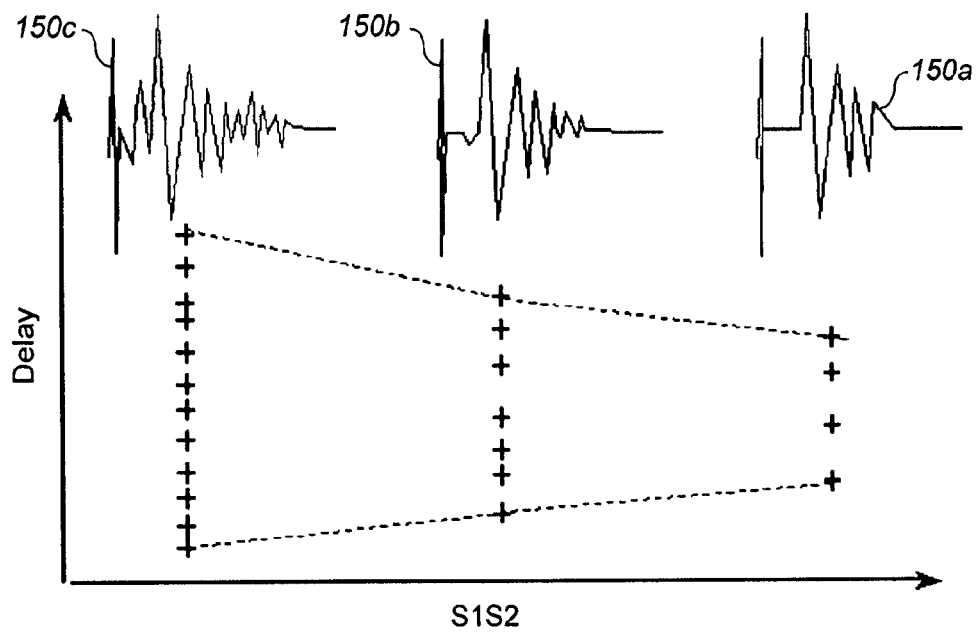
FIG. 19 shows an example of multiple further electrogram traces are used to plot a conduction curve.
Figure 20:
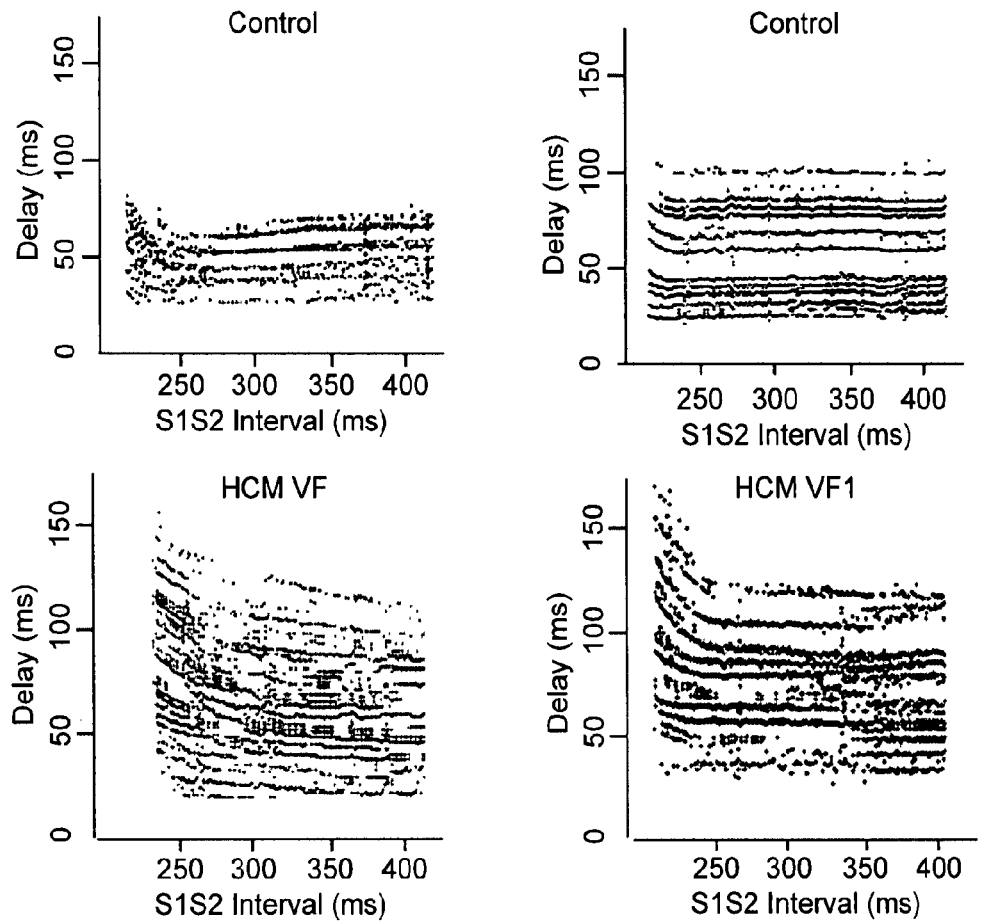
FIG. 20 shows examples of conduction curves plotted for various patients.

FIG. 19 shows the peaks of three electrograms 150a, 150b, 150c, plotted as a function of delay against S1S2 coupling interval. This gives a "conduction curve", i.e. a graphical representation of the speed of conduction though the heart at different S1S2 coupling intervals. FIG. 20 shows four examples of conduction curves plotted over a range of values of the S1S2 coupling interval. Thus, graphs of the S1S2 coupling interval (x axis), plotted against time delay for the signal to reach the other electrodes (y axis), can be plotted for different patients. Such a representation is referred to as paced electrogram fractionation analysis (PEFA); in the present specification this is also referred to as a conduction curve.

PEFA graphs for patients with a history of VF show increasing fractionation (more horizontal lines are shown on the graph): the maximum delay increases as the coupling interval gets shorter; the spread of delays is greater and the spread increases as the coupling interval gets shorter; and the VERP is higher. These latter characteristics of the graph seem to be due to the fact that as the frequency of the pulses increases, an increasing number of cells will be refractory when the signal reaches them; as a result, progress of an activation front, such as the activation front 22 shown in FIGS. 1 to 8 will be delayed as described above with reference to FIGS. 1 to 8.

Figure 21:
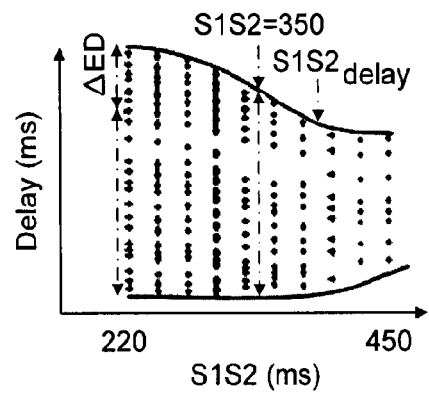
FIG. 21 shows an example of how a conduction curve is analysed.

A known method of analysis of a conduction curve will now be described with reference to FIGS. 21 and 22. FIG. 21 shows a conduction curve on which various parameters are marked. The parameter S1S2$_{delay}$ indicates the value of S1S2 at which the fractionation begins to increase, and ΔED is a measure of an increase in delay over a given S1S2 interval. In this example ΔED relates to the increase in fractionation between an S1S2 of 350 ms and 5 ms above the VERP. Results of the values of ΔED against S1S2$_{delay}$ for a number of different conduction curves, constructed using electrograms from different patients, can be represented graphically, and such a graph is shown on FIG. 22. The points presented on FIG. 22 identify the type of patient to which the results relate. It is possible to construct a line, such as the line A, which enables a basic analysis of the risk of VF. This line A is defined as a linear quantity, known as "discriminant line", indicative of a basic VF risk. For convenience this line is defined as a "fractionation" of 60 ms. It should be noted that the quantity fractionation having the units of time, is different from what is meant by the term fractionation above (this being indicative of the splitting of the lines shown on a PEFA graph). If a point (and thus patient) lies to the right of the line, the patient corresponding to the point tends to be at greater risk of VF, and if a point lies to the left of the line, the corresponding patient tends to be at less of at risk of VF.

Figure 22:
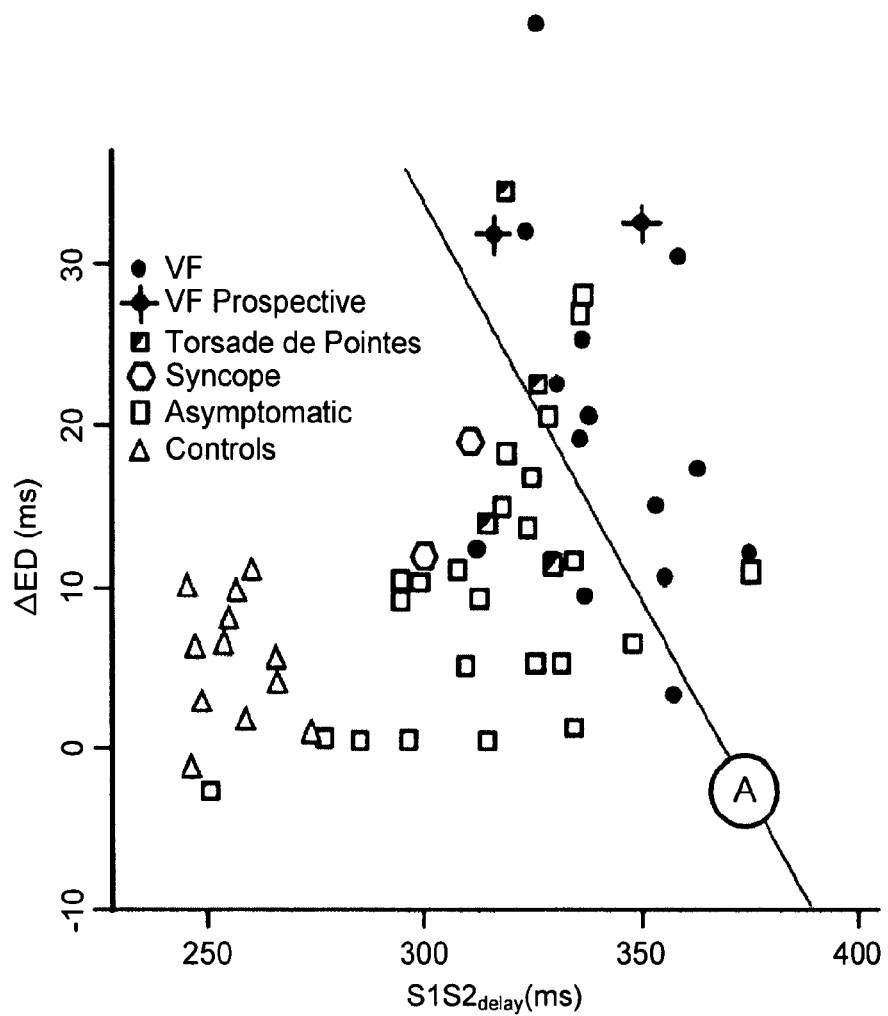
FIG. 22 shows a scattergram of a reduction of the analysis of conduction curves.
Figure 23:
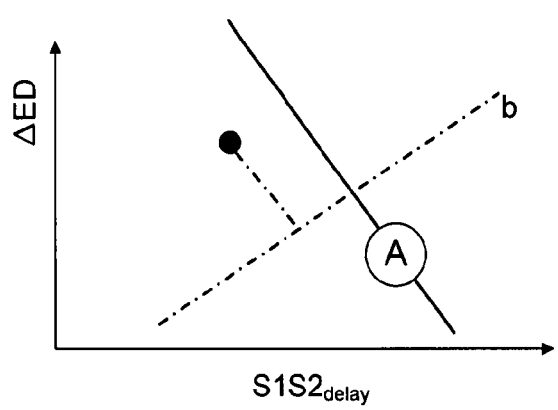
FIG. 23 shows an example of a first method of analysis of a conduction curve.

As mentioned above, LQTS patients show a longer QT interval (i.e. the interval between the QRS complex and the end of the T wave in an electrogram), and in order to distinguish between VF caused by HCM and LQTS the present inventor has developed a novel analytical technique based upon the representation of FIG. 22. FIG. 23 shows a schematic version of the graph of FIG. 22, showing how each point is analysed to determine the linear quantity fractionation assigned to each point, according to this technique.

Referring to FIG. 23, the technique involves constructing a normal b to the line A; each point is then projected onto the normal, and its distance from the line A along the normal is determined. Thus, the distance of each point from the line A, measured normally to line A is determined. This distance represents the fractionation of that patient, relative to the risk threshold of 60 ms of fractionation.

Since the line A has been defined as a single quantity indicative of risk, the distance of a point from line A, i.e. the fractionation of a point, can be used to determine whether other factors show a correlation in the likelihood of VF. For example, since patients having LQTS show a long QT interval it may be that there is a correlation with the length of the QT interval with the risk of VF.

Figure 24:
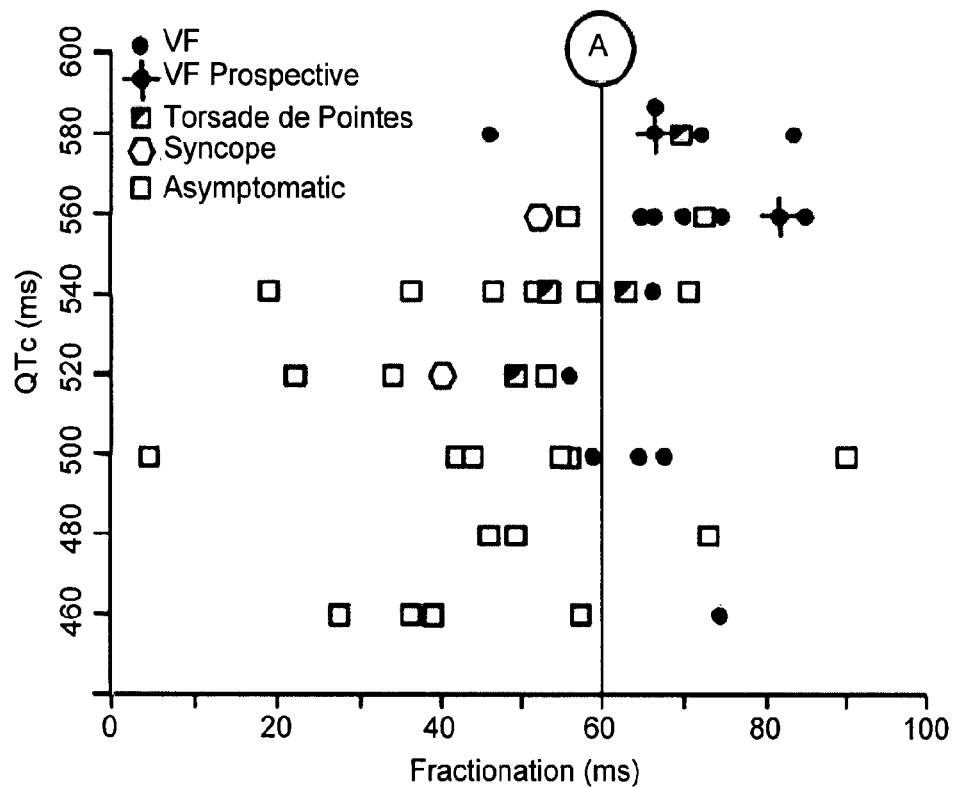
FIG. 24 shows a graph plotted from analysis of a conduction curve according to the first method.

In an attempt to identify risk of VF for patients with QT, the inventor has investigated the relationship between fractionation and the QT interval, corrected according to the rate of the heartbeat, according to Bazett's formula:

$$QTc = \frac{QT}{\sqrt{RR}},$$

where QTc is the QT interval corrected for rate, and RR is the interval from the onset of one QRS complex to the onset of the next QRS complex, measured in seconds. Such a relationship is shown in FIG. 24. Surprisingly, the graph shown in FIG. 24 does not show a significant correlation of VF risk with QTc, since the VF patients are scattered vertically. Therefore the inventor has developed a further novel analysis technique, involving quantification of rate of increase of delay and being based upon conduction curves, such as those introduced with reference to FIG. 20.

An example of how the rate of increase of delay can be measured will now be described with reference to FIG. 25, which shows conduction curves of an LQTS patient, and an HCM patient. Two straight lines 200a, 200b and 210a, 210b are matched to the upper line of the respective conduction curves (these lines are shown as dotted, and are elevated for clarity) by means of, for example, piecewise fitting and continuous analysis of the straight lines 200a, 200b and 210a, 210b. The angle α between the two lines for each graph is measured, and it can be seen from inspection of FIG. 25 that the angle for LQTS patients differs from that associated with HCM patients.

Figure 26:
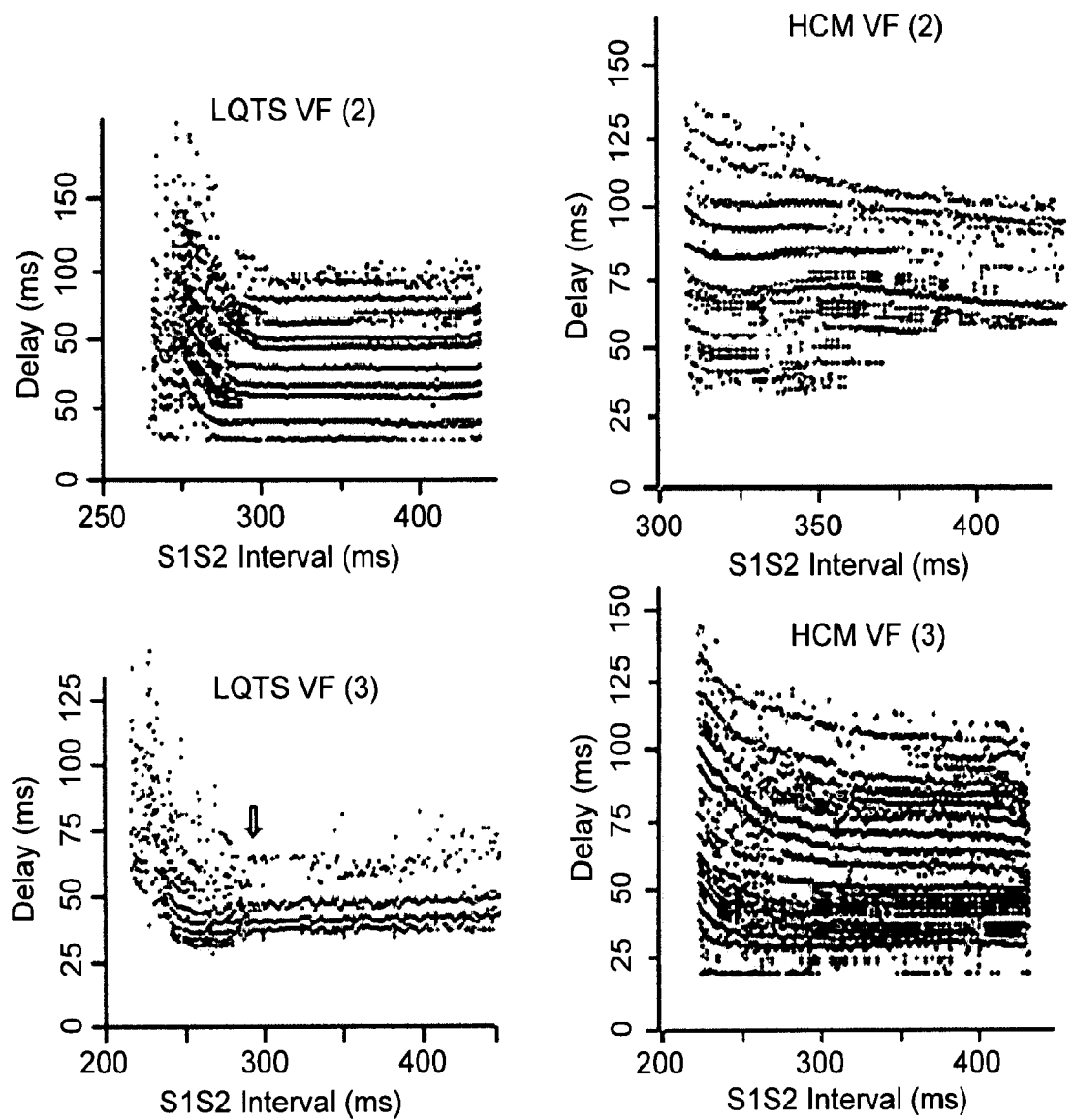
FIG. 26 shows further conduction curves, which can be analysed in the same way.

FIG. 26 shows further examples of conduction curves from LQTS VF and LQTS patients. As can be seen from this Figure, there is a variation in conduction curves from patients having the same disease. In particular, a large variation can be seen between the three conduction curves for the HCM patients. These graphs illustrate that it can be non-trivial to identify a cardiac condition from merely looking at the graphs without performing an analysis.

Figure 27:
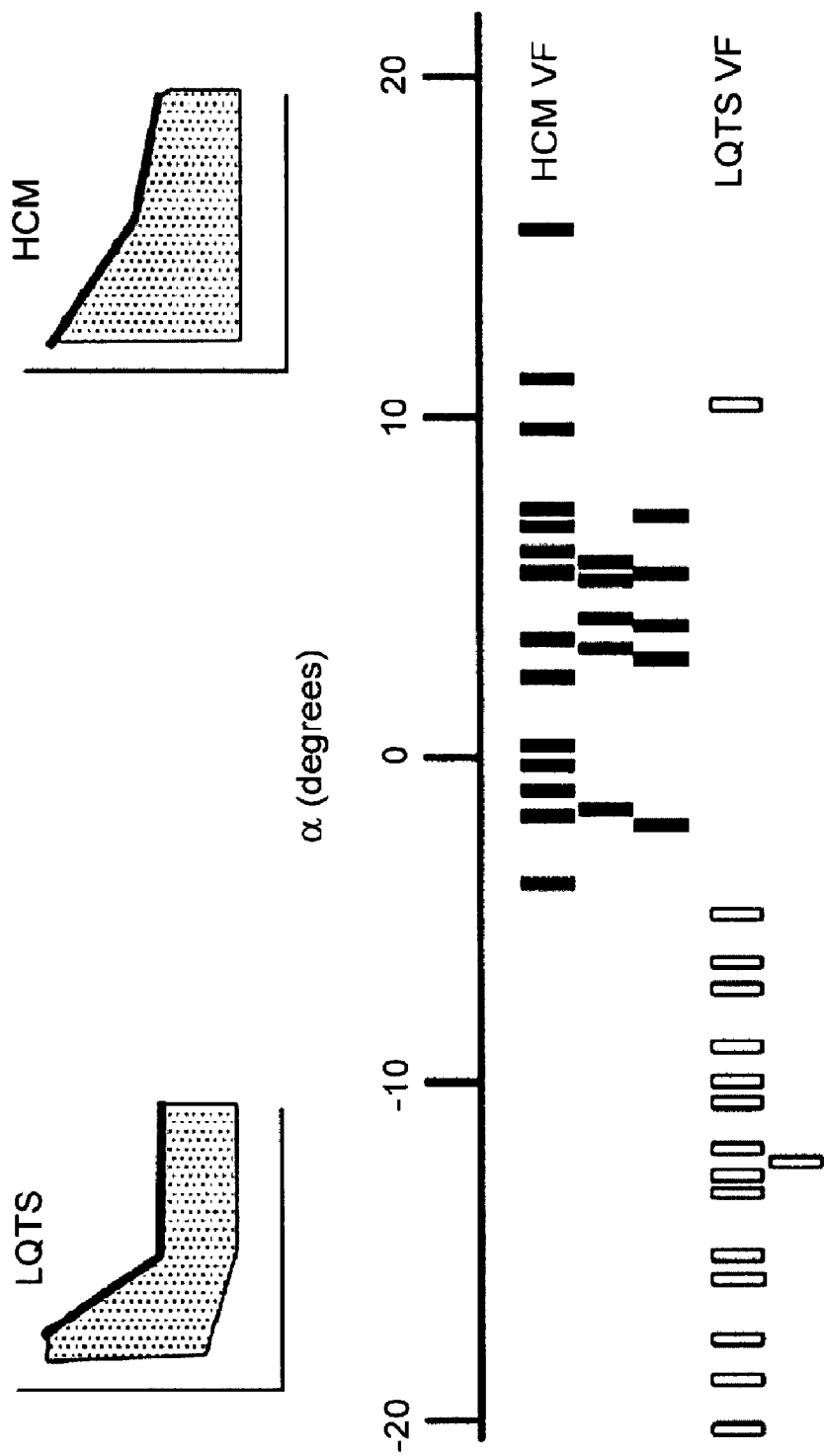
FIG. 27 shows some results obtained by the second method of analysis of various conduction curves.

Once the values of the angle α have been determined they are compared with a known value. This known value may be calculated from a sample population of patients present in a certain experiment, for example, or may be pre-determined. In the current example an average of the values of α for different patients is taken, the values of α for each of these patients is shown on a scale, and the patients are identified by whether they have HCM or LQTS, such as the scale shown in FIG. 27. As can be seen in FIG. 27, there is a clear difference of the values of α in HCM patients and in LQTS patients, indicative of the fact that this method of analysis is useful for determining VF risk in relation to the cardiac condition of the patient.

This process can be automated, or parts of the process can be automated, and other parts can be performed manually.

The value of α gives a measure of danger of VF in a patient, as does the value of the quantity of fractionation associated with that patient which can be identified using prior-art methods. However, α gives information over and above that which can be obtained merely from a consideration of the quantity of fractionation. For example, if a graph were plotted having the quantity fractionation on the abscissa and the value of α on the ordinate for a number of different VF patients, the points would be grouped together horizontally, indicating that the patients have similar values of the quantity of fractionation, but they would be spread vertically, and the points relating to patients having the same cardiac conditions would tend to clump. This vertical spread could also be measured.

Figure 25:
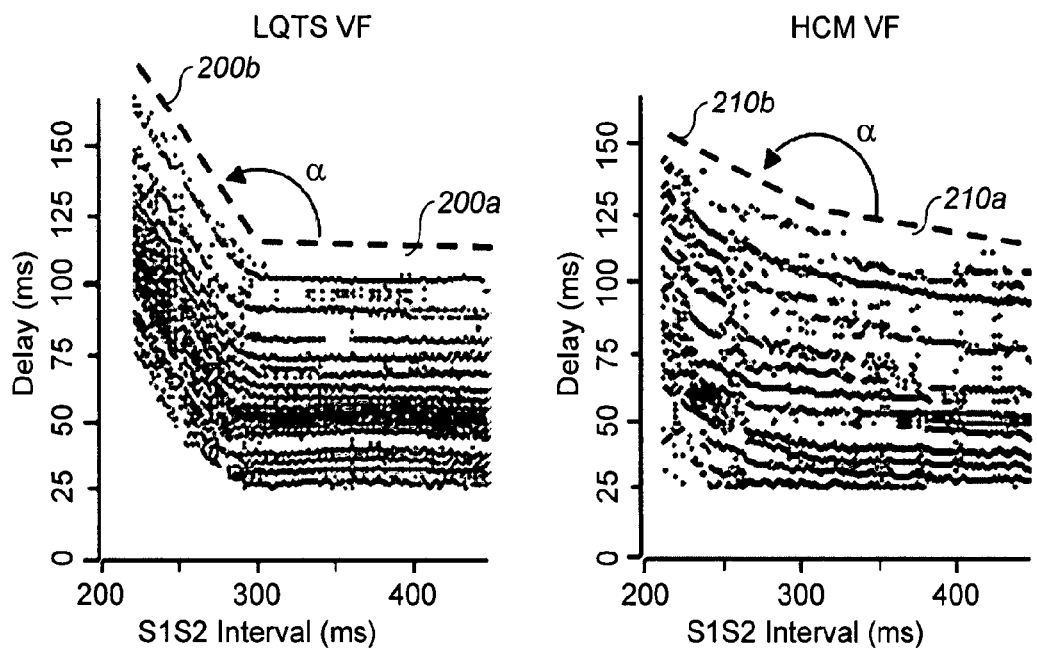
FIG. 25 shows an example of a second method of analysis of a conduction curve.

In addition to the methods discussed in relation to FIGS. 25 and 27 an analysis of the rate of increase of delay over a given range of S1S2 coupling could be measured by using the absolute angle α between the two piecewise continuous lines. In this case, values of α below approximately 150° indicate LQTS, and values of α above approximately 150° indicate HCM. More specifically, angles between approximately 115° and 135° indicate LQTS and angles between approximately 155° and 170° indicate HCM.

The conduction curves can be analyzed using a single line passing through the points, and measuring the angle between this angle and the axis. As a further alternative or additionally, a measurement of the gradient can be taken, and differences in the gradient at different values of S1S2 coupling interval can be determined.

Figure 28:
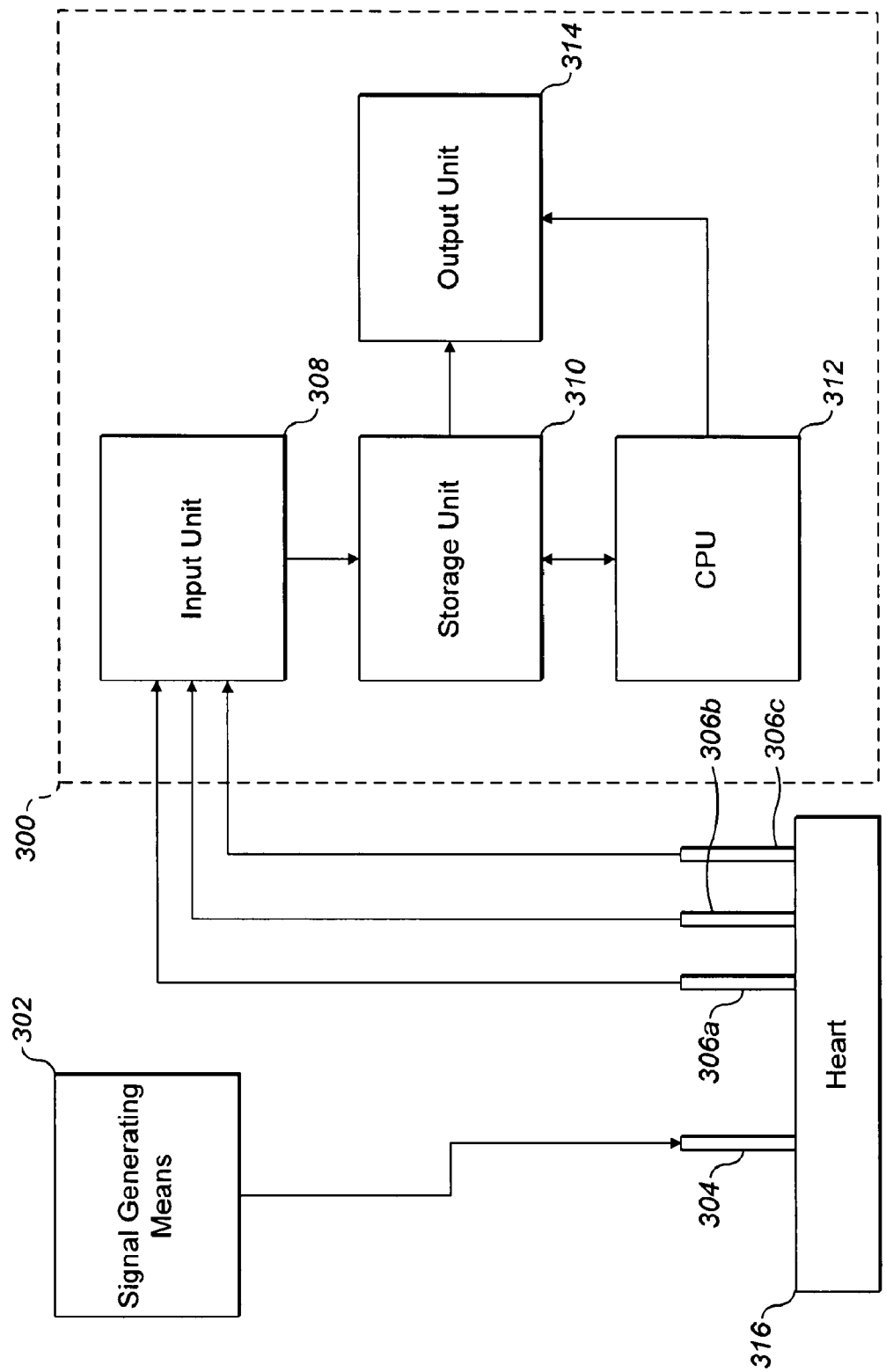
FIG. 28 is a schematic diagram showing a system for performing the analysis shown in FIG. 27.

The value of a for DCM is similar to that of HCM, and the value of a for CHF is roughly in between the values corresponding to HCM and LQTS. FIG. 28 shows a system comprising a computer system or processing system 300 for use in performing the analysis described in relation to FIGS. 25 and 27. The system comprises a signal generator 302 connected to an input electrode 304. Three output electrodes 306a, 306b, and 306c (in this example) are connected to an input unit 308 of the processing system 300. The input unit 308 is connected to a storage unit 310, which is in turn connected to a CPU 312. The CPU 312 and the storage unit 310 are connected to an output unit 314. In use, the input electrode 304 and the three output electrodes 306a, 306b, 306c are inserted into a heart 316, as shown, and the signal generating means 302 generates a pulsed input signal, which passes to the input electrode 304, and to the heart 316. The output electrodes 306a, 306b, 306c detect the output signals, which are sent to the input unit 308 of the processing system 300. The detected signal can then be stored in the storage unit 310, and passes to the CPU 312. The CPU 312 filters the signal, and may apply a series of templates to the signal to further filter the signal, as discussed above. The CPU 312 then performs the analysis discussed above, and sends the results of the analysis to the output unit 314. As shown in FIG. 28 the constituent parts of the processing system 300 can be configured as separate units or as a suite of software running on respective units. Alternatively, the processing system 300 may comprise a single unit, having similar functionality. Furthermore, FIG. 28 shows three output electrodes, whereas more or fewer electrodes could be used.

Figure 29:
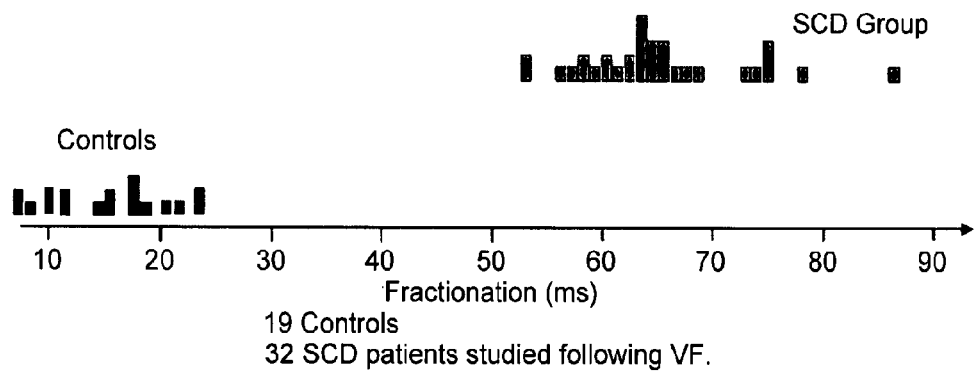
FIG. 29 shows some results obtained by the first method of analysis of various conduction curves.
Figure 30:
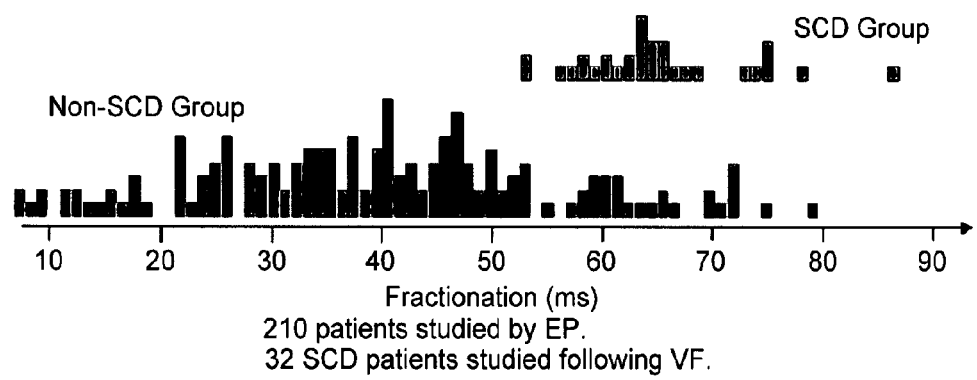
FIG. 30 shows some results obtained by the first method of analysis of various conduction curves.
Figure 31:
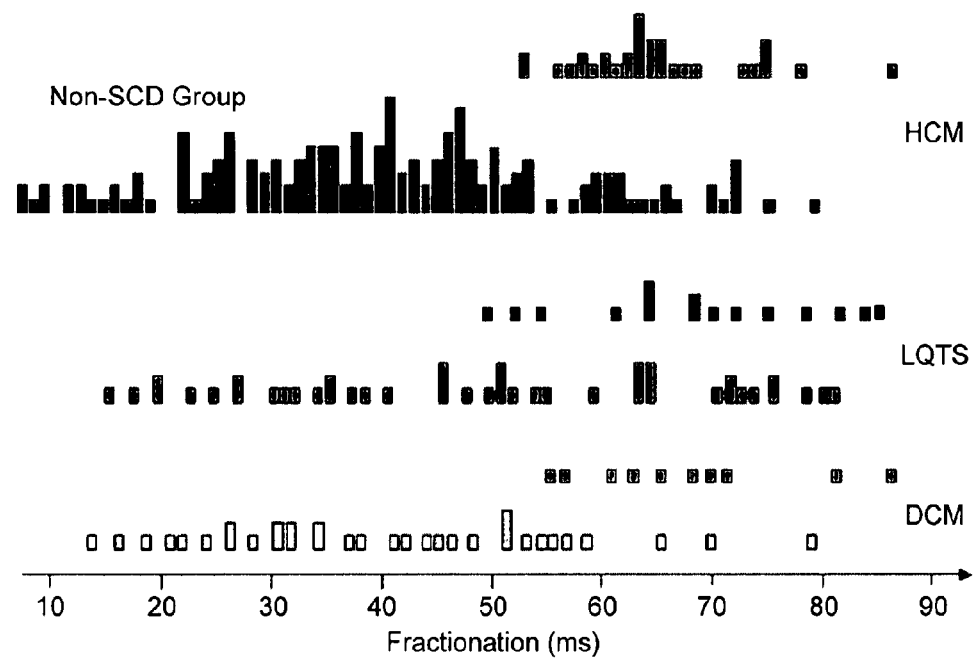
FIG. 31 shows some results obtained by the first method of analysis of various conduction curves.
Figure 32:
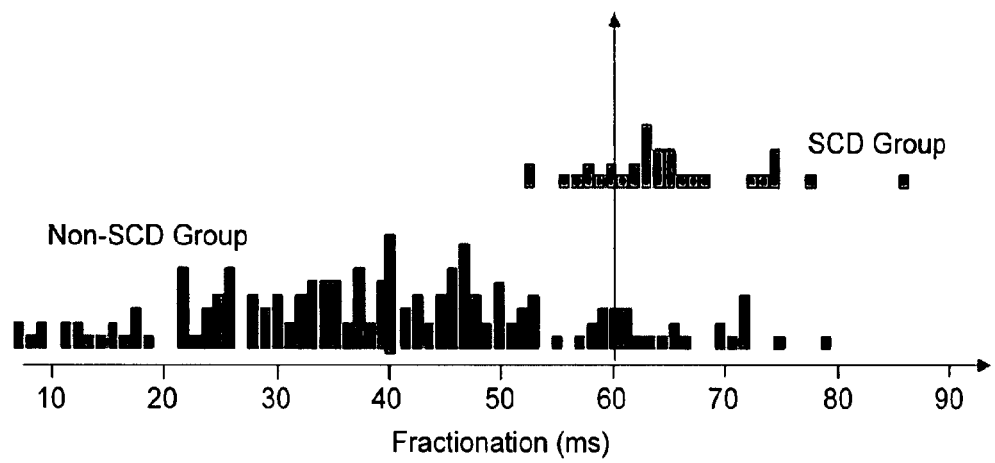
FIG. 32 shows some results obtained by the first method of analysis of various conduction curves.

The "fractionation" value, discussed above in relation to FIGS. 22 and 23 can be used alone as a guide to the risk of an individual to VF. Some graphs of fractionation value for various groups of patients are shown on FIGS. 29 to 33. FIG. 29 shows the fractionation values of a control group compared with an SCD group and FIG. 30 shows the fractionation of a non-SCD group compared with an SCD group. FIG. 31 shows the fractionation of groups having various cardiac conditions, namely HCM, LQTS, and DCM compared with each other and with a non-SCD group.

Figure 33:
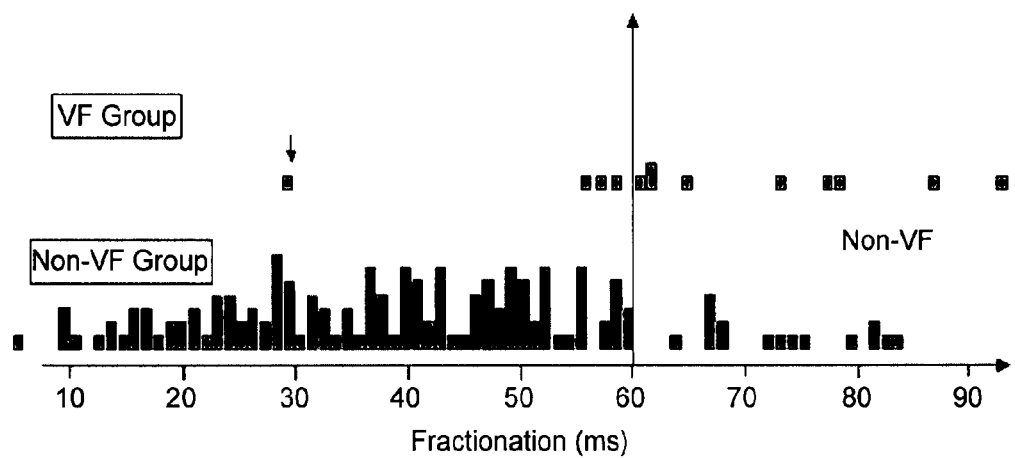
FIG. 33 shows some results obtained by the first method of analysis of various conduction curves.

FIG. 31 shows the graph of FIG. 30 with a line indicative of a fractionation of 60 ms. Further, FIG. 33 shows a graph of a VF group compared with a non-VF group, with a line showing a fractionation of 60 ms. This latter Figure represents a prospective study, i.e. the patients were first studied, and subsequently followed to determine whether any displayed symptoms of a cardiac condition. Thus, these Figures show the fractionation exhibited by the hearts of various patients relative to the fractionation of 60 ms. As discussed above, this gives a basic linear measurement of risk, and a fractionation of 60 ms is indicative of the threshold for risk; a patient exhibiting a fractionation above 60 ms is likely to be prone to VF.

Analysis by Increasing the S1S2 Coupling Interval

As described above, the experiments were conducted by starting the stimulation at a relatively long S1S2 coupling interval, and decreasing the coupling interval. However, the experiment can be conducted by starting with a relatively short S1S2 interval, for example, below 250, 300 or 350 ms and increasing the coupling interval to above 350 ms. This approach has the advantage that the potential effects of abnormal blood flow to the heart on the experimental results could be eliminated. This is due to the fact that starting with a long S1S2 interval and decreasing this may lead to ischemia, or a lack of blood flow to the heart, after a period of time. This means that the results for a shorter S1S2 interval, which are produced after the heart has been subjected to the stimulation for some time, may be affected by effects to do with the blood flow. Running the experiment starting with a short S1S2 interval minimises this effect, since the data for the delay at short S1S2 in this case is collected before the blood flow to the heart is significantly affected by the applied stimulus. This would confirm the conclusion that the characteristics of the graph, such as increased delay and increased fractionation at short S1S2 intervals, is a electrophysiological effect, rather than being blood-flow related.

Analysis Using a Second Premature Extrastimulus

As described above, the pulsing sequence used in the experiments comprises an S1S1 pulse at a constant coupling interval, followed by a premature extrastimulus pulse, S2, where the S1S2 coupling interval is variable. Other pulsing sequences can be used. For example, a pulsing sequence having a further premature extrastimulus pulse, S3, can be used. In this case, the S1S2 coupling interval could be kept constant, and/or the S1S3 coupling interval could be kept constant, while the coupling interval of the other extrastimulus varies. The advantage of including a further premature extrastimulus is that the heart becomes stressed sooner. This has the advantage that the effects associated with a risk of VF may be seen sooner, or at a longer premature stimulus coupling interval. In place of a conduction curve, such as the one shown in FIG. 19 above, a conduction surface can be plotted. For example the conduction surface could be plotted having delay on the z axis, S1S2 coupling interval on the x axis, and S1S3 coupling interval on the y axis.

The conduction surface can be analysed in a similar way to the conduction curves of FIG. 25, as follows: a plane or a series of planes, parallel to respective planes normal to the surface can be constructed. A line of intersection between respective planes can then be determined. An analysis of the properties of this line (such as the equation of the line, or the gradient of the line, or where two or more lines cross, if there are more than one line) can be made in order to identify a cardiac condition.

Further, it is possible to increase the duration of the pulsing sequence, so that more pulses are applied to the heart. This stresses the heart, which may lead to effects associated with VF being shown at longer S1S2 coupling intervals, which improves the safety of the experiment.

Analysis of Post-Coronary Patients

Post-coronary patients, i.e. patients who have had a heart attack, for example a coronary thrombosis which has lead to myocardial infarction (AMI or MI) and scarring of the muscle tissue of the heart, may also be at risk of VF. However, in such patients the scarring or other damage caused to the muscle tissue is generally localized; this is different to the damage associated with HCM or LQTS patients, where the heart muscle tissue instead suffers diffuse damage. This means that electrograms for HCM or LQTS patients can be produced by looking at the left ventricle, for example, and this electrogram can be taken as representative of the rest of the heart. In post-coronary patients the electrogram includes a measurement taken both from the area affected by the heat attack, and from a non-affected region. Therefore, the electrodes can be positioned as discussed above, i.e. having three output electrodes positioned in the right ventricular septum, the inferior wall of the right ventricle and the right ventricular outflow tract, together with an electrode positioned in a region which has been damaged following the coronary thrombosis. Alternatively the electrode in the region which has been damaged may replace one of the other output electrodes.

The above embodiments are to be understood as illustrative examples of embodiments of the invention. It is to be understood that any feature described in relation to any one embodiments may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

The invention claimed is:

1. A system for use in analysis of electrograms, the system comprising:
   a signal generator for generating an input signal;
   an input electrode for applying an input signal to a driving region of a heart organ;
   an output electrode for receiving an output signal at a driven region of the heart organ, so as to record a value thereof;
   a processing system operable to receive signals indicative of said recorded value from the output electrode for analysing conduction paths through the heart organ,
   wherein the signal generator is operable to generate an input signal comprising a plurality of pulses, at least some of the pulses from said plurality being spaced from each other by a pacing interval;
   and wherein the processing system is arranged to identify signal delay between the input signal and the output signal on the basis of the signal received by the output electrode in relation to the plurality of pulses,
   wherein the processing system is arranged to identify a rate of variation in signal delay over a range of values of pacing interval.

2. A system according to claim 1, wherein said processing system is arranged to identify first and second rates of variation in signal delay within the range of values of pacing interval.

3. A system according to claim 2, wherein said processing system is further arranged to compare the first and second rates of variation in signal delay so as to generate a parameter having a value indicative of a difference in said first and second rates of variation in signal delay.

4. A system according to claim 3, wherein said processing system is further arranged to compare said parameter with at least one known parameter value, so as to identify one of a plurality of physiological cardiac conditions.

5. A system according to claim 3, wherein said processing system is arranged to use the output signal so as to construct a graphical representation of output potential against the pacing interval, and said first and second rates of variation in signal delay relate to said graphical representation.

6. A system according to claim 5, wherein said first and second rates of signal delay relate to the gradient of a first portion of the graphical representation, and the gradient of a second portion of the graphical representation, respectively.

7. A system according to claim 6, wherein said parameter is derived from a relative angle between the gradient of the first portion of the graphical representation, and the gradient of the second portion of the graphical representation.

8. A system according to claim 7, wherein if said parameter value is lower than 150° a first physiological cardiac condition is identified and, if said parameter value is higher than approximately 150°, a second physiological cardiac condition is identified.

9. A system according to claim 7, wherein if said parameter value is between approximately 115° and 135° a first physiological cardiac condition is identified and, if said parameter value is between approximately 155° and 170°, a second physiological cardiac condition is identified.

10. A system according to claim 3, wherein said processing system is further arranged to compare said parameter value with an average parameter value, and wherein, if said parameter value is lower than said average parameter value, a first physiological cardiac condition is identified and, if said parameter value is higher than said average parameter, a second physiological cardiac condition is identified.

11. A system according to claim 3, wherein the processing system is arranged to identify a rate of variation in signal delay over a range of values of pacing interval for a plurality of heart organs, and wherein said processing system is further adapted for:
   deriving a respective said parameter value for said plurality of heart organs, to give a plurality of parameter values;
   defining an average of said plurality of parameter values, to give an average parameter value; and
   comparing said average parameter value to a parameter value from a heart organ,
   wherein, if said parameter value is lower than said average parameter value, a first physiological cardiac condition is identified and, if said parameter value is higher than said average parameter value, a second physiological cardiac condition is identified.

12. A system according to claim 8, wherein the first physiological cardiac condition is long QT syndrome.

13. A system according to claim 8, wherein the second physiological cardiac condition is hypertropic cardiomyopathy.

14. A method of analysis of electrograms, the method comprising the steps of:
   generating an input signal;
   applying an input signal to a driving region of a heart organ;
   receiving an output signal at a driven region of the heart organ, so as to record a value thereof;

receiving signals indicative of said recorded value from the output electrode for analysing conduction paths through the heart organ, wherein the input signal comprises a plurality of pulses, at least some of the pulses from said plurality being spaced from each other by a pacing interval;

and wherein the method further comprises the steps of identifying signal delay between the input signal and the output signal on the basis of the output signal received in relation to the plurality of pulses, wherein the method further comprises the steps of identifying a rate of variation in signal delay over a range of values of pacing interval.

* * * * *